(12) United States Patent
Nielsen et al.

(10) Patent No.: US 12,381,013 B2
(45) Date of Patent: Aug. 5, 2025

(54) PREDICTING TOLERABILITY IN AGGRESSIVE NON-HODGKIN LYMPHOMA

(71) Applicants: GENENTECH, INC., South San Francisco, CA (US); HOFFMANN-LA ROCHE INC., Little Falls, NJ (US)

(72) Inventors: Tina Geritz Nielsen, Basel (CH); Joseph Nathaniel Paulson, South San Francisco, CA (US); Daniel Jay Schneider, Wynnewood, PA (US); Edward Jean Bataillard, Welwyn Garden City (GB); Carl Wilson Harris, III, South San Francisco, CA (US); Carsten Henneges, South San Francisco, CA (US); Yoonha Choi, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 212 days.

(21) Appl. No.: 18/156,909

(22) Filed: Jan. 19, 2023

(65) Prior Publication Data
US 2023/0154626 A1   May 18, 2023

Related U.S. Application Data

(63) Continuation of application No. PCT/US2021/070958, filed on Jul. 26, 2021.
(Continued)

(51) Int. Cl.
*G16H 50/50* (2018.01)
*G16H 20/10* (2018.01)
*G16H 50/30* (2018.01)

(52) U.S. Cl.
CPC ............ *G16H 50/50* (2018.01); *G16H 20/10* (2018.01); *G16H 50/30* (2018.01)

(58) Field of Classification Search
CPC ........ G16H 50/50; G16H 20/10; G16H 50/30; G16H 10/20; G16H 50/20; A61K 39/3955; A61P 35/02; C07K 16/2887
See application file for complete search history.

(56) References Cited

U.S. PATENT DOCUMENTS

| | | | | |
|---|---|---|---|---|
| 9,773,094 | B1 * | 9/2017 | Balagere | G06Q 10/06395 |
| 10,740,437 | B1 * | 8/2020 | Shannon | G16H 10/60 |
| 2012/0179481 | A1 * | 7/2012 | Patel | G06Q 30/02 |
| | | | | 705/2 |

FOREIGN PATENT DOCUMENTS

| | | |
|---|---|---|
| JP | 2975137 A1 | 1/2016 |
| WO | WO-2019144116 A1 * 7/2019 | ............ G06F 40/58 |

OTHER PUBLICATIONS

Hyman DM, Eaton AA, Gounder MM, Pamer EG, Pettiford J, Carvajal RD, Ivy SP, Iasonos A, Spriggs DR. Predictors of early treatment discontinuation in patients enrolled on Phase I oncology trials. Oncotarget. Aug. 7, 2015;6(22):19316-27. doi (Year: 2015).*

(Continued)

*Primary Examiner* — Eliza A Lam
(74) *Attorney, Agent, or Firm* — Kilpatrick Townsend & Stockton LLP

(57) ABSTRACT

Systems and methods described herein improve outcomes of subjects with lymphoma. Subjects with lymphoma may be able to avoid conventional treatments that have a high probability of leading to an adverse effect in the subject. Systems and methods allow for a more accurate prediction of subjects who cannot tolerate a particular treatment. Methods may include accessing an input data set that includes multiple input data values pertaining to a particular subject with lymphoma. The method may further include inputting the input data set into a machine-learning model to generate a score corresponding to the degree to which the particular subject will tolerate a particular treatment. The method may (Continued)

include outputting a prediction of the tolerance of the particular subject to the particular treatment using the generated score.

20 Claims, 34 Drawing Sheets

Related U.S. Application Data

(60) Provisional application No. 63/111,777, filed on Nov. 10, 2020, provisional application No. 63/060,371, filed on Aug. 3, 2020.

(56) References Cited

OTHER PUBLICATIONS

Hyman et al., "Predictors of Early Treatment Discontinuation in Patients Enrolled on Phase I Oncology Trials", Online available at: https://www.ncbi.nlm.nih.gov/pmc/articles/PMC4662493/pdf/oncotarget-06-19316.pdf, Oncotarget, vol. 6, No. 22, Feb. 17, 2015, pp. 19316-19327.

Maiolo et al., "Time-To-Event Prediction Applying Artificial Intelligence on End-of-Treatment FDG-PET/CT in Diffuse Large B-Cell Lymphoma", Elsevier Science Publishers, Amsterdam, vol. 7, No. Supplement 1, Apr. 1, 2019, (Abstract).

PCT/US2021/070958, "International Search Report and Written Opinion", Dec. 13, 2021, 15 pages.

\* cited by examiner

| Variable | Value | Events | Total events | Odds ratio (95% CI) |
|---|---|---|---|---|
| Components of TRAIL | | | | |
| Albumin (g/L) | <LLN<br>≥LLN | 56<br>76 | 282<br>740 | 2.16 (1.48-3.15) |
| Creatinine clearance (mL/min) | <LLN<br>≥LLN | 76<br>58 | 382<br>669 | 2.62 (1.81-3.79) |
| CCI score | >2 (median)<br>≤2 (median) | 69<br>65 | 340<br>711 | 2.53 (1.75-3.66) |
| Cardiovascular/diabetes medical history | Present<br>Absent | 39<br>95 | 194<br>857 | 2.02 (1.33-3.02) |
| Bone marrow lymphocytes (%) | Continuous | 89 | 760 | 3.96 (0.40-29.89) |

| | | | |
|---|---|---|---|
| 53 | HYBRID.OUTCOME ~ log(NOIMPF13005) + sqrt(NOIMPPTM) + CMCNT | 557 | 0.60054723 |
| 54 | HYBRID.OUTCOME ~ sqrt(NOIMPIGG) + log(NOIMPCD3LY) + NOIMPOTHCA | 387 | 0.61459941 |
| 55 | HYBRID.OUTCOME ~ sqrt(NOIMPTPROT) + NOIMPF13011^-0.3) + sqrt(NOIMPCD3LY) + QLQC30_NV + I(NOIMPLYMPH^-0.8) + sqrt(NOIMPMONOS) + I(NOIMPCALCIUM^-0.4) + NOIMPWBC + NOIMPCD3LY | 756 | 0.67981707 |
| 56 | HYBRID.OUTCOME ~ NOIMPF13011LY + NOIMPIGG + JUN20.ANY + log(NOIMPALBUM) + sqrt(NOIMPNEUTSP) + sqrt(NOIMPF13005) | 237 | 0.69939024 |
| 57 | HYBRID.OUTCOME ~ NOIMPF13011LY + NOIMPIGG + JUN20.ANY + log(NOIMPALBUM) + sqrt(NOIMPNEUTSP) | 237 | 0.69568415 |
| 58 | HYBRID.OUTCOME ~ NOIMPF13011LY + NOIMPIGG + JUN20.ANY + log(NOIMPRBC) + log(NOIMPALBUM) + sqrt(NOIMPNEUTSP) + sqrt(NOIMPF13005) + log(NOIMPLDH) | 236 | 0.70143995 |
| 59 | HYBRID.OUTCOME ~ I(NOIMPCRCL^-1) + log(NOIMPHGB) + log(NOIMPPALBUM) + CHARLSON + sqrt(NOIMPHCRIT) + I(NOIMPRBC^0.1) | 1021 | 0.70484371 |
| 60 | HYBRID.OUTCOME ~ sqrt(NOIMPRBC) + log(NOIMPCD3LY) | 759 | 0.59201409 |
| 61 | HYBRID.OUTCOME ~ I(NOIMPCRCL^-1) + log(NOIMPHGB) + MHCNT + log(NOIMPALBUM) | 1021 | 0.69264069 |
| 62 | HYBRID.OUTCOME ~ sqrt(NOIMPRBC) + MHCNT + log(NOIMPALBUM) | 777 | 0.5678658 |
| 63 | HYBRID.OUTCOME ~ log(NOIMPF13005) + QLQC30_CO | 770 | 0.65752654 |
| 64 | HYBRID.OUTCOME ~ JUN20.HVD + NOIMPPLDH + I(NOIMPPTINR^-0.4) + NOIMPLDH + NOIMPF13005LY | 856 | 0.62279823 |
| 65 | HYBRID.OUTCOME ~ log(NOIMPF13005) + NOIMPCD19LY | 881 | 0.56552851 |
| 66 | HYBRID.OUTCOME ~ sqrt(NOIMPRBC) + NOIMPALBUM + QLQC30_CO + log(NOIMPHGB) + JUN20.HVD + CHARLSON + NOIMPIGA + NOIMPHGB + log(NOIMPTNR) + NOIMPRBC + sqrt(NOIMPCRCLBSA) | 793 | 0.7492623 |
| 67 | HYBRID.OUTCOME ~ JUN20.HVD + NOIMPTPROT + NOIMPF13005LY + I(NOIMPHCRSAT^-0.5) + sqrt(NOIMPPOTAS) | 769 | 0.66896664 |
| 68 | HYBRID.OUTCOME ~ sqrt(NOIMPTPROT) + NOIMPRBC + I(NOIMPF13011^-0.3) + sqrt(NOIMPCD3LY) + QLQC30_NV + I(NOIMPLYMPH^-0.8) + sqrt(NOIMPMONOS) | 753 | 0.67445299 |
| 69 | HYBRID.OUTCOME ~ sqrt(NOIMPTPROT) + NOIMPRBC + sqrt(NOIMPCRCLBSA) | 858 | 0.65525373 |
| 70 | HYBRID.OUTCOME ~ I(NOIMPCRCL^-1) + log(NOIMPHGB) + MHCNT + log(NOIMPALBUM) + CHARLSON + sqrt(NOIMPHCRIT) + I(NOIMPRBC^0.1) + CMCNT + sqrt(NOIMPCRCL) + CMCLASSCNT + NOIMPCHLOR | 947 | 0.70396682 |
| 71 | HYBRID.OUTCOME ~ log(NOIMPF13005) + NOIMPCD19LY + QLQC30_CO | 777 | 0.57927622 |
| 72 | HYBRID.OUTCOME ~ I(NOIMPCRCL^-1) + log(NOIMPHGB) + MHCNT + log(NOIMPALBUM) + CHARLSON + sqrt(NOIMPHCRIT) + I(NOIMPRBC^0.1) + CMCNT | 1021 | 0.70454545 |
| 73 | HYBRID.OUTCOME ~ sqrt(NOIMPRBC) + NOIMPALBUM + QLQC30_CO + log(NOIMPHGB) + log(NOIMPURACID) + CHARLSON + NOIMPIGG | 794 | 0.72647157 |
| 74 | HYBRID.OUTCOME ~ NOIMPF13011LY + NOIMPIGG + JUN20.ANY + log(NOIMPALBUM) + sqrt(NOIMPNEUTSP) | 237 | 0.69568415 |
| 75 | HYBRID.OUTCOME ~ sqrt(NOIMPIGG) + log(NOIMPCD3LY) + sqrt(NOIMPBUN) + NOIMPBASOS) + I(NOIMPF13005LY^-0.1) + QLQC30_FI + I(NOIMPPOTAS^-1.6) | 592 | 0.68889662 |
| 76 | HYBRID.OUTCOME ~ I(NOIMPLYMPH^-0.3) + sqrt(NOIMPCD3LY) + sqrt(NOIMPBUN) + NOIMPTPROT | 374 | 0.55783501 |
| 77 | HYBRID.OUTCOME ~ sqrt(NOIMPIGG) + log(NOIMPCD3LY) + sqrt(NOIMPPOTAS) + NOIMPTPROT | 661 | 0.58657817 |
| 78 | HYBRID.OUTCOME ~ sqrt(NOIMPIGG) + log(NOIMPCD3LY) + sqrt(NOIMPPOTAS) + sqrt(NOIMPBUN) + NOIMPBASOS) + I(NOIMPF13005LY^-0.1) | 658 | 0.64716639 |
| 79 | HYBRID.OUTCOME ~ JUN20.HVD + NOIMPTPROT + NOIMPF13005LY + I(NOIMPHCRSAT^-0.5) | 770 | 0.66752654 |

FIG. 9 (cont.)

| | | | |
|---|---|---|---|
| 80 | HYBRID.OUTCOME ~ sqrt(NOIMP.TPROT) + NOIMP.RBC + ((NOIMP.PF13011^-0.3) + sqrt(NOIMP.PCD3LY) + QLQC30_NV + ((NOIMP.PLYMPH^-0.8) + sqrt(NOIMP.PMONOS) + ((NOIMP.CAL-CUM^-0.4) + NOIMP.WBC + NOIMP.PCD3LY + NOIMP.IGG | 666 | 0.70642706 |
| 81 | HYBRID.OUTCOME ~ log(NOIMP.RBC) + NOIMP.ALBUM | 1021 | 0.654012 |
| 82 | HYBRID.OUTCOME ~ NOIMP.PF13011LY + NOIMP.IGG + JUN20.ANY + log(NOIMP.ALBUM) + DIABETES2 | 744 | 0.67970253 |
| 83 | HYBRID.OUTCOME ~ ((NOIMP.CRCL^-1) + log(NOIMP.HGB) + log(NOIMP.RBC) + MH.CNT + log(NOIMP.ALBUM) + CHARLSON + sqrt(NOIMP.HCRIT) | 1021 | 0.70293486 |
| 84 | HYBRID.OUTCOME ~ (NOIMP.LYMPH^-0.3) + QLQC30_QL2 + NOIMP.CALCIUM + log(NOIMP.PCD3) | 323 | 0.56769031 |
| 85 | HYBRID.OUTCOME ~ JUN20.HVD + NOIMP.TPROT + NOIMP.PF13005LY + ((NOIMP.PCSAT^-0.5) + sqrt(NOIMP.POTAS) | 769 | 0.66899664 |
| 86 | HYBRID.OUTCOME ~ sqrt(NOIMP.PF13005LY) + QLQC30_QL2 + NOIMP.CALCIUM + log(NOIMP.PCD3) | 769 | 0.62775785 |
| 87 | HYBRID.OUTCOME ~ NOIMP.PF13011LY + NOIMP.IGG + JUN20.ANY + log(NOIMP.ALBUM) + sqrt(NOIMP.PNEUTSP) + sqrt(NOIMP.PLDH) + NOIMP.MONOS | 236 | 0.70833333 |
| 88 | HYBRID.OUTCOME ~ NOIMP.PF13011LY + NOIMP.IGG | 760 | 0.51517061 |
| 89 | HYBRID.OUTCOME ~ ((NOIMP.LYMPH^-0.3) + sqrt(NOIMP.PF13005LY) + QLQC30_QL2 + NOIMP.CALCIUM | 323 | 0.56747405 |
| 90 | HYBRID.OUTCOME ~ sqrt(NOIMP.IGG) + log(NOIMP.LDH) + ((NOIMP.PF13005^-0.7) + ((NOIMP.PCRCL^-0.4) + NOIMP.LDH | 668 | 0.6201809 |
| 91 | HYBRID.OUTCOME ~ log(NOIMP.LDH) + ((NOIMP.PF13005^-0.7) + ((NOIMP.PCRCL^-0.4) + NOIMP.LDH | 856 | 0.57776095 |
| 92 | HYBRID.OUTCOME ~ log(NOIMP.RBC) + sqrt(NOIMP.TPROT) + QLQC30_QL2 + NOIMP.CALCIUM + log(NOIMP.PCD3) + NOIMP.HGB | 906 | 0.66992479 |
| 93 | HYBRID.OUTCOME ~ JUN20.HVD + NOIMP.TPROT + NOIMP.PF13005LY | 769 | 0.67056801 |
| 94 | HYBRID.OUTCOME ~ sqrt(NOIMP.TPROT) + NOIMP.RBC + ((NOIMP.PF13011^-0.3) + sqrt(NOIMP.PCD3LY) + QLQC30_NV + ((NOIMP.PLYMPH^-0.8) + sqrt(NOIMP.PMONOS) + ((NOIMP.CAL-CUM^-0.4) + NOIMP.WBC | 858 | 0.64879268 |
| 95 | HYBRID.OUTCOME ~ sqrt(NOIMP.PF13005LY) + QLQC30_QL2 + NOIMP.CALCIUM + log(NOIMP.PCRCLBSA) + CM.CNT + sqrt(NOIMP.PTT) | 756 | 0.67999351 |
| 96 | HYBRID.OUTCOME ~ sqrt(NOIMP.PF13005LY) + QLQC30_QL2 + NOIMP.CALCIUM + log(NOIMP.HGB) + JUN20.HVD + CHARLSON + NOIMP.PCRCLBSA) + log(NOIMP.PCD3LY) + AGE + NOIMP.IGA | 646 | 0.70557029 |
| 97 | HYBRID.OUTCOME ~ log(NOIMP.RBC) + sqrt(NOIMP.TPROT) + NOIMP.RBC + ((NOIMP.PF13011^-0.3) + sqrt(NOIMP.PCD3LY) + QLQC30_CO + log(NOIMP.HGB) + JUN20.HVD + CHARLSON + NOIMP.PCD3LY | 667 | 0.74971645 |
| 98 | HYBRID.OUTCOME ~ log(NOIMP.RBC) + sqrt(NOIMP.ALBUM) + QLQC30_CO + log(NOIMP.HGB) + JUN20.HVD + CHARLSON + NOIMP.PCD3LY | 667 | 0.7300189 |
| 99 | HYBRID.OUTCOME ~ NOIMP.PF13011LY + NOIMP.IGG + JUN20.ANY + log(NOIMP.ALBUM) + sqrt(NOIMP.PNEUTSP) + log(NOIMP.LDH) + NOIMP.MONOS | 236 | 0.70833333 |
| 100 | HYBRID.OUTCOME ~ sqrt(NOIMP.ALBUM) + QLQC30_CO + log(NOIMP.HGB) | 906 | 0.65558564 |
| 101 | HYBRID.OUTCOME ~ log(NOIMP.PCD19LY) + NOIMP.PTT) + sqrt(NOIMP.PTT) | 557 | 0.57125862 |
| 102 | HYBRID.OUTCOME ~ sqrt(NOIMP.TPROT) + NOIMP.RBC + ((NOIMP.PF13011^-0.3) + sqrt(NOIMP.PCD3LY) + QLQC30_NV + ((NOIMP.LYMPH^-0.8) | 759 | 0.67283763 |
| 103 | HYBRID.OUTCOME ~ sqrt(NOIMP.PRBC) + sqrt(NOIMP.ALBUM) + NOIMP.PNEUTNR) + NOIMP.PCRCLBSA) + sqrt(NOIMP.PF13005) + sqrt(NOIMP.PCRCLBSA) + NOIMP.PF13005 | 659 | 0.74444061 |
| 104 | HYBRID.OUTCOME ~ sqrt(NOIMP.RBC) + sqrt(NOIMP.ALBUM) + CHARLSON + sqrt(NOIMP.PCRCLBSA) + NOIMP.IGG + JUN20.ANY | 895 | 0.69784427 |
| 105 | HYBRID.OUTCOME ~ NOIMP.PF13011LY + NOIMP.IGG + JUN20.ANY | 760 | 0.58354831 |
| 106 | HYBRID.OUTCOME ~ ((NOIMP.PCRCL^-1) + log(NOIMP.ALBUM) + CHARLSON + JUN20.HVD + log(NOIMP.PCRCLBSA) + QLQC30_NV | 909 | 0.71167518 |
| 107 | HYBRID.OUTCOME ~ ((NOIMP.PCRCL^-1) + log(NOIMP.ALBUM) + CHARLSON + JUN20.HVD + log(NOIMP.PCRCLBSA) + QLQC30_PA | 909 | 0.71024663 |

| # | Formula | N | Value |
|---|---------|---|-------|
| 297 | HYBRID.OUTCOME ~ I(NOIMPCRCL^-1) + log(NOIMPHGB) + log(NOIMPRBC) + MHCNT + log(NOIMPALBUM) | 1021 | 0.692264099 |
| 298 | HYBRID.OUTCOME ~ sqrt(NOIMPIGG) + log(NOIMPCD3LY) + NOIMPBUN + sqrt(NOIMPPOTAS) + sqrt(NOIMPCD3LY) + NOIMPBUN + sqrt(NOIMPNEUTSP) + sqrt(NOIMPBASOS)) + I(NOIMPF13005LY^0.1) + QLQC30_FI | 156 | 0.72245632 |
| 299 | HYBRID.OUTCOME ~ CHARLSON + log(NOIMPALBUM) + log(NOIMPCRCL) + AGE + sqrt(NOIMPBMLYMP) + log(NOIMPRBC) + I(NOIMPCRCL^-1) | 741 | 0.73738971 |
| 300 | HYBRID.OUTCOME ~ CHARLSON + log(NOIMPALBUM) + log(NOIMPCRCL) + AGE + sqrt(NOIMPIGG) | 891 | 0.70910073 |
| 301 | HYBRID.OUTCOME ~ I(NOIMPCRCL^-1) + log(NOIMPHGB) + log(NOIMPRBC) | 1049 | 0.68164098 |
| 302 | HYBRID.OUTCOME ~ CHARLSON + log(NOIMPALBUM) + log(NOIMPCRCL) + AGE + log(NOIMPF13005) | 855 | 0.68126287 |
| 303 | HYBRID.OUTCOME ~ CHARLSON + log(NOIMPALBUM) + log(NOIMPCD3LY) + AGE + NOIMPHGB + NOIMPF13005LY + log(NOIMPLDH) | 852 | 0.71494794 |
| 304 | HYBRID.OUTCOME ~ CHARLSON + log(NOIMPALBUM) + log(NOIMPCD3LY) + NOIMPF13005LY + log(NOIMPLDH) + sqrt(NOIMPIGG) | 742 | 0.73300211 |
| 305 | HYBRID.OUTCOME ~ CHARLSON + log(NOIMPALBUM) + log(NOIMPCD3LY) + NOIMPF13005LY + log(NOIMPLDH) + NOIMPF13011LY + log(NOIMPF13005) | 742 | 0.73866415 |
| 306 | HYBRID.OUTCOME ~ CHARLSON + log(NOIMPALBUM) + log(NOIMPCRCL) + AGE + sqrt(NOIMPBMLYMP) + log(NOIMPRBC) | 741 | 0.72907659 |
| 307 | HYBRID.OUTCOME ~ sqrt(NOIMPIGG) + log(NOIMPCD3LY) + NOIMPOTHCA + sqrt(NOIMPPOTAS) + sqrt(NOIMPNEUTSP) + sqrt(NOIMPBASOS)) + I(NOIMPF13005LY^0.1) + QLQC30_FI | 156 | 0.72245632 |
| 308 | HYBRID.OUTCOME ~ CHARLSON + log(NOIMPALBUM) + log(NOIMPCRCL) + AGE + sqrt(NOIMPBMLYMP) + log(NOIMPLDH) | 741 | 0.73738971 |
| 309 | HYBRID.OUTCOME ~ CHARLSON + log(NOIMPALBUM) + log(NOIMPCRCL) + AGE + sqrt(NOIMPLDH) | 1018 | 0.71056091 |
| 310 | HYBRID.OUTCOME ~ I(NOIMPCRCL^-1) + log(NOIMPHGB) + log(NOIMPRBC) + MHCNT | 1049 | 0.66796183 |
| 311 | HYBRID.OUTCOME ~ CHARLSON + log(NOIMPALBUM) + log(NOIMPCRCL) + AGE + sqrt(NOIMPBMLYMP) + log(NOIMPRBC) | 741 | 0.72907659 |
| 312 | HYBRID.OUTCOME ~ CHARLSON + log(NOIMPALBUM) + log(NOIMPCRCL) + AGE + NOIMPF13011LY | 855 | 0.66057627 |
| 313 | HYBRID.OUTCOME ~ CHARLSON + log(NOIMPALBUM) + log(NOIMPCRCL) + AGE + sqrt(NOIMPBMLYMP) | 742 | 0.72034746 |
| 314 | HYBRID.OUTCOME ~ I(NOIMPCRCL^-1) + log(NOIMPHGB) + log(NOIMPRBC) + MHCNT + log(NOIMPALBUM) + CHARLSON + sqrt(NOIMPHCRIT) | 1021 | 0.70293486 |
| 315 | HYBRID.OUTCOME ~ CHARLSON + log(NOIMPALBUM) + log(NOIMPCRCL) + AGE + sqrt(NOIMPBMLYMP) | 742 | 0.72034746 |
| 316 | HYBRID.OUTCOME ~ I(NOIMPCRCL^-1) + log(NOIMPALBUM) + log(NOIMPCRCL) + CHARLSON + JUN20.HVD + sqrt(NOIMPBMLYMP) + log(NOIMPCRCLBSA) + AGE | 742 | 0.75437396 |
| 317 | HYBRID.OUTCOME ~ CHARLSON + log(NOIMPALBUM) + log(NOIMPCRCL) + CHARLSON + JUN20.HVD + log(NOIMPCRCLBSA) + sqrt(NOIMPHGB) | 1022 | 0.71241062 |
| 318 | HYBRID.OUTCOME ~ CHARLSON + log(NOIMPALBUM) + log(NOIMPCRCL) + CHARLSON + JUN20.HVD + log(NOIMPCRCLBSA) + sqrt(NOIMPNAPTT) | 294 | 0.69652539 |
| 319 | HYBRID.OUTCOME ~ CHARLSON + log(NOIMPALBUM) + log(NOIMPCRCL^-1) + log(NOIMPCRCL) + log(NOIMPCRCLBSA) + sqrt(NOIMPCRCLBSA) + sqrt(NOIMPHGB) + sqrt(NOIMPNAPTT) | 294 | 0.7025641 |
| 320 | HYBRID.OUTCOME ~ sqrt(NOIMPBMLYMP) + log(NOIMPPTTINR) + qad(NOIMPEOSIN^-1, q:hrf, 12.72006, 32.34774, +Inf)) + NOIMPNEUTR + log(NOIMPCD16) + NOIMPLDH + ANN + NOIMPALT + NOIMPHGB + QAD.QLQC30_DY | 613 | 0.68290851 |
| 321 | HYBRID.OUTCOME ~ CHARLSON + log(NOIMPALBUM) + log(NOIMPCRCL) + AGE + NOIMPHGB + NOIMPCD3LY + NOIMPF13005LY | 855 | 0.72925397 |
| 322 | HYBRID.OUTCOME ~ QAD.QLQC30_FI + NOIMPIGA + I(NOIMPF13005^0.7) + NOIMPF13005 + sqrt(NOIMPF13011) + NOIMPF13011LY) + NOIMPNEUTR + MHCNT + QAD.QLQC30_CF + JUN20.HVD + I(NOIMPF13011^-0.3) + QAD.QLQC30_DY + log(NOIMPPTTINR) + sqrt(NOIMPALT) | 745 | 0.69823293 |
| 323 | HYBRID.OUTCOME ~ CHARLSON + log(NOIMPCRCL) + AGE | 1022 | 0.69473102 |

FIG. 9 (cont.)

| 324 | HYBRID.OUTCOME ~ QAD.QLQC30_FI + NOIMPIGA + I(NOIMPF13005^0.7) + NOIMPF13005 + log(NOIMPF13011) + NOIMPF13011 + sqrt(NOIMPF13011LY) + NOIMPNEUTR + MHCNT + QAD.QLQC30_CF + JUN20.HVD + I(NOIMPF13011^0.3) + QAD.QLQC30_DY + log(NOIMPPTNR) + sqrt(NOIMPALT) | 745 | 0.698623293 |
|---|---|---|---|
| 325 | HYBRID.OUTCOME ~ CHARLSON + log(NOIMPALBUM) + log(NOIMPCRCL) + AGE + NOIMPCD3LY + NOIMPF13005LY + NOIMPRBC + NOIMPCRCLBSA + NOIMPURACID + NOIMP.TPROT + NOIMPLDH + NOIMPHCRIT + NOIMPALT + NOIMPF13011LY + NOIMPCRCL + NOIMPCD19 + NOIMPCALCIUM + NOIMPCHLOR + NOIMPALBUM + NOIMPCD3LY.NOIMPRBC | 774 | 0.75305805 |
| 326 | HYBRID.OUTCOME ~ log(NOIMPF13005) + NOIMPALBUM + I(NOIMPLYMPH.HF^0.3) + sqrt(NOIMPCD16) + log(NOIMPCD16) | 265 | 0.62991308 |
| 327 | HYBRID.OUTCOME ~ sqrt(NOIMPF13005) + log(NOIMPGG) + log(NOIMPCD3LY) + NOIMPTHCA + NOIMPPOTAS) + NOIMPBUN + sqrt(NOIMPNEUTSP) + sqrt(NOIMPBASOS) + I(NOIMPF13005LY^0.1) + QLQC30_FI | 156 | 0.72245632 |
| 328 | HYBRID.OUTCOME ~ log(NOIMPF13005) + NOIMPALBUM + I(NOIMPLYMPH.HF^0.3) + sqrt(NOIMPPTM) + log(NOIMPCD3LY) + NOIMPCD16) + NOIMPCD19LY + sqrt(NOIMPALBUM) + sqrt(NOIMPLDH) + sqrt(NOIMPPOTAS) + sqrt(NOIMPHCRIT) + CMCNT + log(NOIMPALT) + sqrt(NOIMPPTNR) + NOIMPEOSINF | 260 | 0.68636625 |
| 329 | HYBRID.OUTCOME ~ log(NOIMPF13005) + NOIMPALBUM | 855 | 0.61607122 |
| 330 | HYBRID.OUTCOME ~ log(NOIMPF13005) + NOIMPALBUM + I(NOIMPLYMPH.HF^0.3) + sqrt(NOIMPPTM) + log(NOIMPCD16) + NOIMPCD19LY + sqrt(NOIMPALBUM) + sqrt(NOIMPLDH) + sqrt(NOIMPPOTAS) + sqrt(NOIMPHCRIT) | 263 | 0.66316994 |
| 331 | HYBRID.OUTCOME ~ log(NOIMPF13005) + NOIMPALBUM + NOIMPPOTAS | 854 | 0.61533902 |
| 332 | HYBRID.OUTCOME ~ log(NOIMPF13005) + NOIMPALBUM + I(NOIMPLYMPH.HF^0.3) | 368 | 0.61888644 |
| 333 | HYBRID.OUTCOME ~ log(NOIMPF13005) + NOIMPALBUM + I(NOIMPLYMPH.HF^0.3) + sqrt(NOIMPPTM) + log(NOIMPCD19LY + sqrt(NOIMPCD16) + NOIMPCD19LY + sqrt(NOIMPALBUM) + sqrt(NOIMPLDH) + sqrt(NOIMPPOTAS) | 263 | 0.64285714 |
| 334 | HYBRID.OUTCOME ~ log(NOIMPF13005) + NOIMPALBUM + I(NOIMPLYMPH.HF^0.3) + sqrt(NOIMPPTM) + log(NOIMPCD16) + NOIMPCD19LY + sqrt(NOIMPALBUM) + sqrt(NOIMPLDH) + sqrt(NOIMPPOTAS) + sqrt(NOIMPNEUTR) + CMCNT + log(NOIMPEOSINF + NOIMPNEUTR) + NOIMPCD19LY + sqrt(NOIMPAST) + NOIMPLDH + QLQC30_CF + sqrt(NOIMPREC^0.1) + log(NOIMPCD3) + log(NOIMPLATE + I(NOIMPHOSAT^0.5) + NOIMPPLATE + I(NOIMPHOSAT^0.5) + NOIMPCD3 + QLQC30_PA + NOIMPPOTAS | 225 | 0.74849322 |
| 335 | HYBRID.OUTCOME ~ log(NOIMPF13005) + NOIMPALBUM + I(NOIMPLYMPH.HF^0.3) + sqrt(NOIMPPTM) | 265 | 0.62783447 |
| 336 | HYBRID.OUTCOME ~ log(NOIMPF13005) + NOIMPALBUM + I(NOIMPLYMPH.HF^0.3) + sqrt(NOIMPPTM) + log(NOIMPCD16) + NOIMPCD19LY + sqrt(NOIMPALBUM) + sqrt(NOIMPLDH) + sqrt(NOIMPPOTAS) + sqrt(NOIMPPTNR) + NOIMPEOSINF + QLQC30_CF | 233 | 0.68710919 |
| 337 | HYBRID.OUTCOME ~ log(NOIMPF13005) + NOIMPALBUM + I(NOIMPLYMPH.HF^0.3) + sqrt(NOIMPPTM) + log(NOIMPCD16) + NOIMPCD19LY + sqrt(NOIMPALBUM) + sqrt(NOIMPLDH) + sqrt(NOIMPPOTAS) + sqrt(NOIMPHCRIT) + CMCNT + log(NOIMPALT) | 263 | 0.67785619 |

FIG. 9 (cont.)

```
Table: HYBRID.OUTCOME, ts=5, r=50

response              teamsize   variable                    vs         vs.var
-----------------     --------   ------------------------   ---------  ---------
HYBRID.OUTCOME           5       I(NOIMP.CRCL^-1)           18.201288  0.0612620
HYBRID.OUTCOME           5       log(NOIMP.HGB)             15.453680  0.0413941
HYBRID.OUTCOME           5       log(NOIMP.RBC)             13.504530  0.0266455
HYBRID.OUTCOME           5       MHCNT                      13.107149  0.0550596
HYBRID.OUTCOME           5       log(NOIMP.ALBUM)           12.957611  0.0490376
HYBRID.OUTCOME           5       CHARLSON                   12.627306  0.0489623
HYBRID.OUTCOME           5       sqrt(NOIMP.HCRIT)          12.492996  0.0496513
HYBRID.OUTCOME           5       I(NOIMP.RBC^0.1)           12.434658  0.0565232
HYBRID.OUTCOME           5       CMCNT                      12.181955  0.0312631
HYBRID.OUTCOME           5       sqrt(NOIMP.CRCL)           11.775794  0.0253692
HYBRID.OUTCOME           5       CMCLASSCNT                 11.625513  0.0584349
HYBRID.OUTCOME           5       NOIMP.CHLOR                10.915339  0.0220220
HYBRID.OUTCOME           5       QLQC30_PF2                 10.913639  0.0535323
HYBRID.OUTCOME           5       NOIMP.F13005               10.563397  0.0474837
HYBRID.OUTCOME           5       I(NOIMP.F13005LY^-0.1)     10.339705  0.0297634
HYBRID.OUTCOME           5       NOIMP.HGB                  10.241674  0.0351584
HYBRID.OUTCOME           5       DIABETES2                  10.210141  0.0275800
HYBRID.OUTCOME           5       AGE                         9.934790  0.0656831
HYBRID.OUTCOME           5       QLQC30_SF                   9.667702  0.0416380
HYBRID.OUTCOME           5       sqrt(NOIMP.CD3)             9.501054  0.0830043
```

FIG. 10

```
Table: HYBRID.OUTCOME, ts=15, r=50

response          teamsize   variable                     vs         vs.var
---------------   --------   ----------------------   ----------   ----------
HYBRID.OUTCOME       15      log(NOIMP.NEUTSA)         13.554907    0.0131692
HYBRID.OUTCOME       15      sqrt(NOIMP.TPROT)         12.277489    0.0173883
HYBRID.OUTCOME       15      NOIMP.RBC                 11.064526    0.0068807
HYBRID.OUTCOME       15      I(NOIMP.F13011^-0.3)      10.854354    0.0105132
HYBRID.OUTCOME       15      sqrt(NOIMP.CD3LY)          9.971907    0.0065273
HYBRID.OUTCOME       15      QLQC30_NV                  9.356048    0.0117444
HYBRID.OUTCOME       15      I(NOIMP.LYMPH^-0.8)        9.316340    0.0073425
HYBRID.OUTCOME       15      sqrt(NOIMP.MONOS)          9.204459    0.0181628
HYBRID.OUTCOME       15      I(NOIMP.CALCUM^-0.4)       8.939260    0.0101786
HYBRID.OUTCOME       15      NOIMP.WBC                  8.498788    0.0136087
HYBRID.OUTCOME       15      NOIMP.CD3LY                8.276291    0.0109158
HYBRID.OUTCOME       15      NOIMP.IGG                  8.221193    0.0071625
HYBRID.OUTCOME       15      I(NOIMP.HCRIT^0.1)         7.707065    0.0064863
HYBRID.OUTCOME       15      NOIMP.NEUTSP               7.498756    0.0139923
HYBRID.OUTCOME       15      QLQC30_FA                  7.433544    0.0073173
HYBRID.OUTCOME       15      I(NOIMP.F13005LY^-0.1)     7.431944    0.0082063
HYBRID.OUTCOME       15      log(NOIMP.IGM)             6.999680    0.0063104
HYBRID.OUTCOME       15      log(NOIMP.AST)             6.728614    0.0060393
HYBRID.OUTCOME       15      NOIMP.BMLYMP               6.473318    0.0105463
HYBRID.OUTCOME       15      EXTRANODAL                 6.382251    0.0072334
```

FIG. 11

```
Table: HYBRID.OUTCOME, ts=10, r=50

response            teamsize   variable                       vs        vs.var
----------------    --------   -----------------------  ----------  ----------
HYBRID.OUTCOME            10   sqrt(NOIMP.IGG)           12.286367   0.0134838
HYBRID.OUTCOME            10   log(NOIMP.CD3LY)          11.844501   0.0132307
HYBRID.OUTCOME            10   NOIMP.OTHCA               11.761373   0.0188963
HYBRID.OUTCOME            10   sqrt(NOIMP.POTAS)         11.614287   0.0107829
HYBRID.OUTCOME            10   sqrt(NOIMP.CD3LY)         11.230011   0.0484514
HYBRID.OUTCOME            10   NOIMP.BUN                 11.138134   0.0325336
HYBRID.OUTCOME            10   sqrt(NOIMP.NEUTSP)        11.082448   0.0130542
HYBRID.OUTCOME            10   sqrt(NOIMP.BASOS)         10.766112   0.0228466
HYBRID.OUTCOME            10   I(NOIMP.F13005LY^-0.1)     9.978693   0.0147091
HYBRID.OUTCOME            10   QLQC30_FI                  9.391734   0.0263448
HYBRID.OUTCOME            10   I(NOIMP.POTAS^-1.6)        9.026910   0.0278747
HYBRID.OUTCOME            10   I(NOIMP.LYMPHF^-0.3)       9.007306   0.0111622
HYBRID.OUTCOME            10   log(NOIMP.POTAS)           8.924302   0.0108240
HYBRID.OUTCOME            10   NOIMP.PTINR                8.658611   0.0314112
HYBRID.OUTCOME            10   sqrt(NOIMP.PLATE)          8.386380   0.0179017
HYBRID.OUTCOME            10   NOIMP.SODIUM               8.340156   0.0271756
HYBRID.OUTCOME            10   I(NOIMP.NEUTSP^-0.2)       7.721191   0.0125996
HYBRID.OUTCOME            10   sqrt(NOIMP.BICARB)         7.664618   0.0088188
HYBRID.OUTCOME            10   log(NOIMP.NEUTSA)          7.482049   0.0219800
HYBRID.OUTCOME            10   sqrt(NOIMP.SODIUM)         7.466525   0.0130279
```

FIG. 12

```
Table: HYBRID.OUTCOME, ts=15, r=50

response          teamsize   variable                      vs          vs.var
---------------   --------   ----------------------    ----------   ----------
HYBRID.OUTCOME         15    I(NOIMP.LYMPHF^-0.3)       12.651675    0.0044465
HYBRID.OUTCOME         15    sqrt(NOIMP.F13005LY)       11.261392    0.0079914
HYBRID.OUTCOME         15    NOIMP.TPROT                11.193280    0.0104153
HYBRID.OUTCOME         15    QLQC30_QL2                  9.789120    0.0081427
HYBRID.OUTCOME         15    NOIMP.CALCUM                9.269393    0.0142535
HYBRID.OUTCOME         15    log(NOIMP.CD3)              9.151594    0.0151388
HYBRID.OUTCOME         15    NOIMP.HGB                   9.119338    0.0063050
HYBRID.OUTCOME         15    sqrt(NOIMP.CRCLBSA)         8.850509    0.0104893
HYBRID.OUTCOME         15    CMCNT                       8.579465    0.0114706
HYBRID.OUTCOME         15    sqrt(NOIMP.PTT)             8.227506    0.0085902
HYBRID.OUTCOME         15    QLQC30_FI                   8.066865    0.0077561
HYBRID.OUTCOME         15    sqrt(NOIMP.LYMPHF)          7.734572    0.0103853
HYBRID.OUTCOME         15    I(NOIMP.HCRIT^0.1)          7.389048    0.0055790
HYBRID.OUTCOME         15    I(NOIMP.WBC^-1.4)           7.363675    0.0070179
HYBRID.OUTCOME         15    sqrt(NOIMP.EOSINF)          7.300652    0.0089190
HYBRID.OUTCOME         15    sqrt(NOIMP.URACID)          7.018358    0.0043040
HYBRID.OUTCOME         15    NOIMP.CD16                  6.857975    0.0106617
HYBRID.OUTCOME         15    sqrt(NOIMP.NEUTSA)          6.850617    0.0131884
HYBRID.OUTCOME         15    NOIMP.CD19LY                6.753653    0.0154409
HYBRID.OUTCOME         15    SEX                         6.583772    0.0118663
```

FIG. 13

```
Table: HYBRID.OUTCOME, ts=6, r=50

response              teamsize   variable                  vs         vs.var
-----------------     --------   --------------------   ----------   ----------
HYBRID.OUTCOME           6       log(NOIMP.RBC)          16.148368    0.0582400
HYBRID.OUTCOME           6       sqrt(NOIMP.RBC)         13.896957    0.0256756
HYBRID.OUTCOME           6       NOIMP.ALBUM             13.287001    0.0284818
HYBRID.OUTCOME           6       QLQC30_CO               13.232362    0.0593146
HYBRID.OUTCOME           6       log(NOIMP.HGB)          13.050980    0.0235081
HYBRID.OUTCOME           6       log(NOIMP.CRCLBSA)      12.246446    0.0419438
HYBRID.OUTCOME           6       JUN20.HVD               12.109980    0.0525958
HYBRID.OUTCOME           6       sqrt(NOIMP.URACID)      11.701605    0.0350523
HYBRID.OUTCOME           6       CHARLSON                11.413735    0.0263029
HYBRID.OUTCOME           6       NOIMP.IGG               10.984591    0.0208548
HYBRID.OUTCOME           6       log(NOIMP.CD3LY)        10.972742    0.0379881
HYBRID.OUTCOME           6       sqrt(NOIMP.F13005LY)    10.844195    0.0455341
HYBRID.OUTCOME           6       AGE                     10.136440    0.0527578
HYBRID.OUTCOME           6       NOIMP.IGA                9.260972    0.0401960
HYBRID.OUTCOME           6       NOIMP.HGB                9.005414    0.0376269
HYBRID.OUTCOME           6       log(NOIMP.PTINR)         8.975300    0.0230089
HYBRID.OUTCOME           6       NOIMP.RBC                8.825026    0.0480306
HYBRID.OUTCOME           6       sqrt(NOIMP.CRCLBSA)      8.799473    0.0262749
HYBRID.OUTCOME           6       I(NOIMP.RBC^0.1)         8.361371    0.0193962
HYBRID.OUTCOME           6       NOIMP.F13005             8.246613    0.0599302
```

FIG. 14

PREDICTING TOLERABILITY IN AGGRESSIVE NON-HODGKIN LYMPHOMA

CROSS-REFERENCE TO RELATED APPLICATIONS

The present application is a continuation of International Application No. PCT/US2021/070958, entitled "PREDICTING TOLERABILITY IN AGGRESSIVE NON-HODGKIN LYMPHOMA," filed on Jul. 26, 2021, and claims priority to U.S. Provisional Patent Application 63/060,371, entitled "PREDICTING TOLERABILITY OF R-CHOP IN AGGRESSIVE NON-HODGKIN LYMPHOMA," filed on Aug. 3, 2020, and U.S. Provisional Patent Application 63/111,777, entitled "PREDICTING TOLERABILITY OF R-CHOP IN AGGRESSIVE NON-HODGKIN LYMPHOMA," filed on Nov. 10, 2020, the entire contents of all of which are incorporate herein by reference for all purposes.

FIELD

Methods and systems disclosed herein relate generally to determining whether certain treatments for diffuse large B-cell lymphoma are likely to be tolerated by a particular subject rather than determining whether such treatments are likely to be effective. For example, an outcome score can be computed using a machine-learning model to predict a clinical outcome of treating a particular subject with R-CHOP (rituximab, cyclophosphamide, doxorubicin hydrochloride, vincristine, prednisolone).

BACKGROUND

R-CHOP (rituximab, cyclophosphamide, doxorubicin hydrochloride, vincristine, prednisolone) remains the standard of care for first-line (1 L) treatment of diffuse large B-cell lymphoma (DLBCL), with a long-term event free survival of 60-70% in subjects who complete the recommended treatment course of 6-8 cycles (Coiffier et al, Blood 2010). However, a significant portion of subjects are unable to tolerate R-CHOP due to (for example) comorbidity or frailty, which confers susceptibility to consequences of treatment-related toxicities. These subjects are less likely to achieve complete remission and are at higher risk of relapse as they receive a lower chemotherapy dose intensity due to treatment discontinuation, interruptions, or reductions (Długosz-Danecka et al, Cancer Med 2019). Identifying these subjects upfront could facilitate treatment, thereby sparing them the unfavorable risk/benefit profile of R-CHOP treatment. Identifying tolerability of treatments other than R-CHOP in subjects is also desired. This disclosure addresses these and other needs.

SUMMARY

In some embodiments, systems and methods are provided that relate to building and using a machine-learning model to accurately predict whether a subject will tolerate a particular treatment for lymphoma. Tolerating the particular treatment can mean not suffering an adverse event, include death and hospitalization, as a result of the particular treatment rather than progression of lymphoma. Specifically, the model may be built and used to predict whether a subject diagnosed with diffuse large B-cell lymphoma (DLBCL) will tolerate anti-CD20 treatment with CHOP (Cyclophosphamide, Hydroxydaunorubicin [Doxorubicin], Oncovin [Vincristine], Prednisone) and/or R-CHOP (rituximab, cyclophosphamide, doxorubicin hydrochloride, vincristine, prednisolone) as a treatment. The machine-learning model, TRAIL (Tolerability of R-CHOP In Aggressive non-Hodgkin Lymphoma), transforms values for a set of clinical variables to predict immunochemotherapy tolerability in subjects with previously untreated DLBCL. Results generated from the machine-learning model can be output to help physicians identify subjects who are at high risk of not tolerating R-CHOP-based therapies. If a model result predicts that a subject will not tolerate an R-CHOP therapy, the physician may opt to consider, recommend, or provide an alternative therapy. The model may be particularly important for geriatric subjects, both with and without comorbidities. Geriatric subjects may be less likely to tolerate R-CHOP, but identifying geriatric subjects that can tolerate the R-CHOP treatment can lead to improved clinical outcomes over withholding treatment from subjects over a certain age. Predicting the tolerability of a treatment of DLBCL, rather than merely predicting an effectiveness of the treatment, provides for improved clinical outcomes for subjects who might otherwise suffer an adverse event as a result of treatment. Methods of predicting tolerability of a particular treatment, systems that perform the method, and computer program products storing the method are described.

In one aspect, a method includes accessing an input data set that includes multiple input data values pertaining to a particular subject with lymphoma. Each input data value corresponds to a variable of a set of variables. The method includes inputting the input data set into a machine-learning model to generate a score corresponding to the degree to which the particular subject will tolerate a particular treatment. Tolerating the particular treatment may include not having the particular treatment ended or reduced below a threshold dose within a time period after starting the particular treatment. The machine-learning model includes a set of parameters determined using multiple training data elements. Each of the multiple training data elements corresponds to a training subject. Each of the multiple training data elements include a training input data set and a label. The label indicates a tolerance of the training subject to the particular treatment. A function relates received input data sets and the parameters to the score. The method includes outputting a prediction of the tolerance of the particular subject to the particular treatment using the generated score.

In some embodiments, the set of variables in the method may include a result from a blood panel. The set of variables may include a characterization of a medical history of the particular subject. The method may include sending a request to a computing system storing the medical history of the particular subject. The method may include receiving the medical history of the particular subject. The method may further include determining an index value characterizing comorbidities of the particular subject, where the index value is an input data value of the multiple data values.

In some embodiments, the set of variables may include a result from an invasive diagnostic. In some embodiments, the set of variables may include an albumin concentration, a creatinine clearance, a comorbidity index, or a presence of cardiovascular or diabetes medical history. The set of variables may further include a level of bone marrow lymphocytes.

In some embodiments, the set of variables may include 5 or fewer, 10 or fewer, or 15 or fewer variables. The set of variables may include a level of hemoglobin, a red blood cell count, a hematocrit, concomitant medication count, a level of chloride, a total level of CD3 and CD4 protein complexes and T cell co-receptors, a level of lymphocytes, or a level of CD3 protein complex and T cell co-receptor.

In some embodiments, the lymphoma may be diffuse large B-cell lymphoma. The particular treatment may include administration of rituximab, cyclophosphamide, doxorubicin hydrochloride, vincristine, and prednisolone. The particular treatment may include cyclophosphamide or doxorubicin hydrochloride.

In some embodiments, the method may further include using a blood panel to process a blood sample from the particular subject to determine one or more input data values of the multiple input data values.

In some embodiments, the time period for not ending or reducing the particular treatment below the threshold dose is 18 weeks or less.

In some embodiments, the prediction is the particular subject is unlikely to tolerate the particular treatment.

In some embodiments, the method may further include comparing the score to a cutoff value, where the cutoff value is determined from a plurality of reference subjects. Each reference subject of the plurality of reference subjects may have a respective predicted score. The cutoff value may be determined to achieve a predefined level of sensitivity or a predefined level of specificity for predicting tolerance of the particular treatment in the plurality of reference subjects.

In some embodiments, the method may further include identifying a subset of the plurality of reference subjects. A respective score of each reference subject in the subset may be lower than a score of each reference subject in the plurality of reference subjects but not in the subset. A size of the subset may correspond to a predefined percentage relative to a size the plurality of reference subjects. The method may further include defining the cutoff value as a given value that separates respective scores of reference subjects in the subset from scores of reference subjects in the plurality of reference subjects but not in the subset. Comparing the score to the cutoff value may include determining that the score exceeds the cutoff value. The prediction may be that the particular subject is unlikely to tolerate the particular treatment.

In some embodiments, the method may further include in response to returning the prediction that the particular subject is unlikely to tolerate the particular treatment, outputting a recommendation to enroll the particular subject in a clinical study including a treatment different than the particular treatment.

In some embodiments, the method may include returning the prediction that the particular subject is unlikely to tolerate the particular treatment, outputting a recommendation to not administer the particular treatment to the particular subject.

In some embodiments, the score may be a probability of the particular subject tolerating the particular treatment.

In one aspect, a computer-implemented method includes training a machine-learning model to predict whether a particular subject having lymphoma will tolerate a particular treatment. The method includes accessing a training data set that includes multiple training data elements. Each of the multiple training data elements corresponds to a training subject with lymphoma. Each of the multiple training data elements includes a training input data set and a label. The label indicates a tolerance of the training subject to a particular treatment. The training subject tolerated the particular treatment when the particular treatment is not ended or reduced below a threshold dose within a time period after starting the particular treatment. The method includes training a machine-learning model to generate a score corresponding to the degree to which a particular subject will tolerate the particular treatment using the training data set. Training the machine-learning model includes learning a set of parameters, and determining a function relating the set of parameters to the score.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures:

FIG. 7 shows a table of odds ratios for baseline characteristics association with the hybrid outcome according to some embodiments of the present disclosure, and although most of the components listed are divided into two categories of values (e.g., <LLN and ≥LLN for albumin), the values for the variables are on a continuous scale, not a binary scale;

FIG. 9 lists models for predicting tolerability according to some embodiments of the present disclosure;

FIG. 10 lists the top variables in models with 5 variables according to some embodiments of the present disclosure;

FIG. 11 lists the top variables in models with 15 variables according to some embodiments of the present disclosure;

FIG. 12 lists the top variables in models with 10 variables according to some embodiments of the present disclosure;

FIG. 13 lists the top variables in models with 15 variables according to some embodiments of the present disclosure;

FIG. 14 lists the top variables in models with 6 variables according to some embodiments of the present disclosure;

Figure 1:
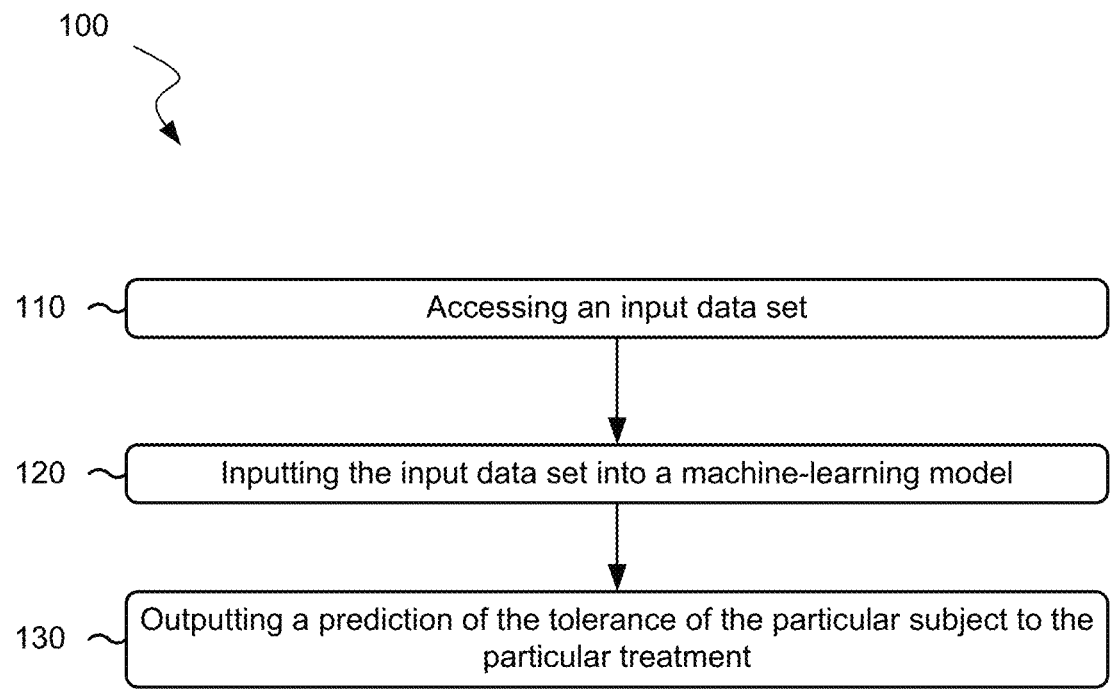
FIG. 1 is a process for using a machine-learning model to predict tolerability of a particular treatment in a particular subject according to some embodiments of the present disclosure.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

Models have been previously developed to predict the effectiveness of a particular treatment for disease such as lymphoma. These models can help determine whether a particular treatment will effectively treat a subject's lymphoma. However, in some cases, a particular treatment may actually be harmful to some subjects. For example, even if a treatment effectively treats the subject's lymphoma, it may trigger an adverse event that results in a harm (e.g., net harm) to the subject. The particular treatment in certain subjects may lead to death, hospitalization, or serious illness. Avoiding such negative outcomes is desirable. Models that determine whether a particular subject can tolerate a particular treatment for lymphoma, rather than the effectiveness of a particular treatment, have not been previously developed.

Systems and methods have been developed to predict whether a subject will tolerate a particular treatment. A machine-learning model, using existing datasets, is trained to predict whether a subject can tolerate a particular treatment for lymphoma. The machine-learning model may include a relatively small number of easily obtainable variables and accurately predict which subjects will tolerate or not tolerate a particular treatment.

Accurately predicting tolerability of a particular treatment in subjects improves outcomes of subjects with lymphoma. Subjects with lymphoma who have a high probability of an adverse effect related to a treatment may be able to avoid conventional treatments and undesirable clinical outcomes. The machine-learning models developed result in a more accurate method to predict adverse effects in subjects than conventional prognostic indicators, such as age IPI (International Prognostic Index), or ECOG PS (Eastern Cooperative Oncology Group Performance Status).

For subjects newly diagnosed subjects with diffuse large B-cell lymphoma (DLBCL), rituximab in combination with cyclophosphamide, doxorubicin, vincristine and prednisolone (R-CHOP) is the standard first-line treatment. Treatment with cycles of R-CHOP has been demonstrated to be efficacious for the majority of subjects.

While R-CHOP has been the mainstay of DLBCL treatment for more than two decades, this regimen is associated with significant toxicity. Many subjects with DLBCL, especially those who are geriatric, present with a reduced physiologic reserve and often comorbidities that may preclude full dose R-CHOP. Among subjects aged over 66 years with newly diagnosed non-Hodgkin's lymphoma in the Surveillance, Epidemiologic, and End Results (SEER)-Medicare database, 52% of subjects had one or more comorbidity and 26% had a Charlson Comorbidity Index greater than 2. The most prevalent comorbidities were diabetes (25%), chronic obstructive pulmonary disease (16%), and congestive heart failure (12%). In a retrospective cohort study of approximately 18,000 subjects aged 66 years and older, diagnosed with DLBCL between 2001-2013 in the SEER-Medicare database, subjects over 80 years of age were reported to be less likely to receive R-CHOP as a first line of therapy compared with subjects aged 66 to 80 years (46.5% in subjects >80 years versus 71% in subjects up to 80 years).

Geriatric subjects with DLBCL may be more vulnerable to toxicity of R-CHOP, but not treating the subjects with R-CHOP also can lead to negative results. Outcomes have been found to be inferior in subjects who do not complete R-CHOP therapy compared to those who complete the therapy. Subjects who cannot complete R-CHOP therapy because they cannot tolerate R-CHOP then are faced with worse outcomes resulting from DLBCL than subjects who can complete the R-CHOP therapy. Identifying subjects that are not likely to tolerate R-CHOP early can improve the likelihood of avoiding adverse events related to R-CHOP and can also provide an opportunity for these subjects to consider clinical studies or other treatments. At the same time, subjects that are predicted to be able to tolerate R-CHOP can have improved clinical outcomes if they receive the complete R-CHOP treatment over those that receive a partial R-CHOP treatment.

The models described herein provide a combination of prognostic performance, clinical utility, and simplicity superior to conventional methods. Certain models include four simple variables, which can all be readily obtained in routine clinical practice. Example variables include Charlson Comorbidity Index, presence of cardiovascular disease or diabetes, low serum albumin, and low creatinine clearance, which are frequently observed in subjects with DLBCL.

Predicting subject outcome during induction treatment is a difficult task. It is evident that not all collected variables contain information useful to evaluate the chance of induction success.

Models developed according to methods disclosed herein can be used as clinical decision support to guide physician judgment. A physician may use the results of the model in combination with clinical tests or other data to determine the course of treatment for the subject. The results of the model may also enable subject enrollment into a clinical study for novel therapies. These novel therapies may be different than and/or may not include all or a portion of components of anti-CD20 or R-CHOP. Some embodiments may also eliminate or reduce anti-CD20 or R-CHOP associated toxicities for subjects having DLBCL who are predicted to be at risk of suffering adverse effects or are predicted to be unlikely to benefit from the treatment. In some embodiments, the model may be used for a subject undergoing a particular treatment to predict tolerability of the subject to the treatment and/or to customize a monitoring approach (e.g., customizing which tests are performed and/or test frequency to promote well-being of the subject).

II. Definitions

CHOP refers to the combination of Cyclophosphamide, Hydroxydaunorubicin [Doxorubicin], Oncovin [Vincristine], and Prednisone.

R-CHOP refers to CHOP with rituximab.

DLBCL refers to diffuse large B-cell lymphoma.

"Biological sample" refers to any sample that is taken from a subject (e.g., a human subject, such as a person having lymphoma. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used.

"Adverse event" or AE refers to an event including death, illness requiring hospitalization, a life-threatening event, or persistent disability or incapacity.

"Tolerate" in terms of a subject tolerating a treatment refers to not having the particular treatment prematurely ended or reduced below a threshold dose (e.g., 80%) as a result of death or other adverse event within a time period after starting treatment. The adverse event is not a result of progression of the lymphoma but rather attributed to or likely to be attributed to some side effect of the particular treatment. The time period may be from 1 to 2, 2 to 4, 4 to 8, 8 to 12, 12 to 16, 16 to 18, 18 to 24, 24 to 30, 30 to 40, 40 to 50, or 50 to 52 weeks. The threshold dose may be 50% to 60%, 60% to 70%, or 70% to 80% of the planned dose. The planned dose may be the dose determined for the subject at the time of diagnosis or prior to a subsequent treatment cycle of the subject (e.g., 1 day before a scheduled treatment). A subject who "tolerates" a particular treatment often refers to a subject that is known to complete the particular treatment above the threshold dose during a certain time period.

"Tolerance" refers to a degree of how well a subject reacts to a particular treatment. A tolerance may be binary to indicate that the treatment was tolerated or not tolerated. In some embodiments, tolerance may be a real number or integer along a scale. For example, a subject that dies from the particular treatment may be considered to have less tolerance for the particular treatment than a subject that has the dose of the treatment reduced to 70% of the planned dose. Tolerance may be a numerical scale (e.g., 0 to 1) or may be discrete classifications (e.g., low, medium, high).

"Tolerability" refers to a likelihood or probability that a subject tolerates a particular treatment. "Tolerability" often refers to the likelihood or probability for a subject before or during treatment, before an adverse event occurs. For example, low "tolerability" may correspond to a high likelihood of unplanned hospitalization or emergency department visit.

"Disease progression" or PD refers to a worsening of the disease, characterized by an increase in disease burden or new lymphoma lesions.

III. Example Methods and Systems for Predicting Tolerability

Methods for predicting tolerability of a particular treatment in a particular subject are described. FIG. 1 shows an exemplary process 100 for using a computational model to predict tolerability.

A subject that does not tolerate a particular treatment has the particular treatment reduced below a threshold dose (e.g., 80%) as a result of an adverse event within a time period after starting treatment or has the particular treatment ended as a result of such hospitalization or death. For example, a subject that does not tolerate a treatment may be one that has at least one of the following events during the first few cycles of the treatment: (1) an adverse event (AE) not being the result of disease progression and the AE leading to withdrawal from the treatment before the completion of the treatment, (2) death not resulting from disease progression (PD), or (3) a decrease in dose intensity resulting in a dose intensity less than a certain threshold, with the decrease not related to disease progression. Chemotherapy is often given at regular intervals, termed "cycles." Typical intervals include every 14, 21, or 28 days.

The particular treatment can include multiple treatment cycles, each of which may be 14 or 21 days long. The number of cycles may be 2, 3, 4, 5, 6, 7, 8, 9, or 10. As examples, for tolerability to CHOP-type treatments, the inability to tolerate the treatment can include an adverse event (AE) leading to withdrawal of cyclophosphamide and/or doxorubicin before completion of a particular number of cycles less than a default number of cycles. For example, an inability to tolerate the treatment may include discontinuing the treatment when fewer than 90%, fewer than 80%, fewer than 70%, fewer than 60%, fewer than 50%, or fewer than 40% of the default number of treatment cycles were completed. As another example, an inability to tolerate the treatment may include discontinuing the treatment when a number of completed cycles is equal to 8 cycles, 6 cycles, 4 cycles, 2 cycles, or 1 cycle when a number of planned cycles in the particular treatment is greater than the number of completed cycles. Additionally, an inability to tolerate the treatment may include death not resulting from disease progression (PD) or the average dose intensity of cyclophosphamide and/or doxorubicin reduced to under 80% for reasons.

At block 110, an input data set that includes multiple input data values pertaining to a particular subject with lymphoma is accessed. The lymphoma may be diffuse large B-cell lymphoma (DLBCL). The particular subject may be a human. The particular subject may be over a certain age, including 60, 65, 70, 75, 80, or 85 years old. The lymphoma may include (for example) non-Hodgkin's lymphoma, Hodgkin's lymphoma, chronic lymphocytic leukemia, cutaneous B-cell lymphoma, cutaneous T-cell lymphoma, or Waldenstrom macroglobulinemia.

Each input data value corresponds to a variable of a set of variables. The set of variables may include a result from a blood panel, including a conventional blood panel or a complete blood count. Blood panel variables may include a level of calcium, carbon dioxide, chloride, creatinine, glucose, potassium, sodium, and/or urea nitrogen. A complete blood count includes a count of each of: red blood cells, white blood cells, hemoglobin, hematocrit, and platelets. In some embodiments, the set of variables may include a characterization of the subject's medical history. For example, a variable may indicate an existence and type of any comorbidities, such as cardiovascular disease or diabetes. The variable may represent a result from an invasive diagnostic, which may include a bone marrow sample or a biopsy. A model controller system, which may include a computer system storing a machine learning model, may access the input data set.

The set of variables may include an albumin concentration (ALBUMIN), a creatinine clearance (CRCL), a comorbidity index (e.g., Charlson comorbidity index [CHARLSON]), a presence of cardiovascular or diabetes medical history (e.g., heart, vascular, and diabetes comorbidities [HVD]), or a combination thereof. In some embodiments, the set of variables may include a combination of all four of these variables. In some embodiments, the set of variables may include a level of bone marrow lymphocytes. The level of bone marrow lymphocytes may be an absolute or normalized count (e.g., concentration, percentage), mass, or volume. The multiple input data values may include 1 to 5, 5 to 10, 10 to 15, or more than 15 values. The multiple input data values may include any value described herein. The value may be a count, a concentration, or an indication of the presence or absence of a component. Example variables include a level of hemoglobin (HGB), red blood cell count (RBC), hematocrit (HCRIT), concomitant medication count (CMCNT), a level of chloride (CHLOR), a total level of CD3 and CD4 protein complexes and T cell co-receptors (F13005), a total level of CD3 and CD4 protein complexes and T cell co-receptors and lymphocytes (F13005LY), age (AGE), and/or level of CD3 protein complexes and T cell co-receptor (CD3). In some embodiments, variables may include results from answering a health questionnaire regarding current quality of life (e.g., QLQC30 available at eortc.org/app/uploads/sites/2/2018/08/Specimen-QLQ-C30-English.pdf (accessed Jul. 12, 2021)).

Process 100 may include obtaining the multiple input data values associated with the particular subject. In some instances, one or more of the multiple input data values correspond to values of one or more laboratory variables. Thus, obtaining the multiple input data values can include running an assay (e.g., blood panel) on a biological sample obtained from the particular subject or receiving data from a computing system associated with a laboratory that ran an assay on a biological sample.

Process 100 may include sending a request to a computing system (e.g., a care provider system associated with a care provider or a laboratory system associated with testing equipment) in order to access the input data set. A portion or all of the input data set may be stored on a laboratory system. The laboratory system may include a computer system that runs or is used to run assays on the particular subject. The laboratory system may store data from an assay run by a technician or medical practitioner. In some embodiments, the care provider system may store a portion or all of the input data set. For example, the care provider system may store a medical history of the particular subject. The medical history of the particular subject may be inputted into the care provider system just before (e.g., within an hour or a day) the input data set is accessed. In some embodiments, the medical history of the particular subject has been inputted in the care provider system over weeks or years with visits of the particular subject to the care provider. The medical history of the particular subject may be received by the model controller system. The received data may optionally be preprocessed. For example, an identification of one or more comorbidities can be detected within medical record data, and an index value can be generated based on the detection (s). The index value may include a Charlson comorbidity index or an index of heart, vascular, and diabetes comorbidities.

Data from a laboratory system may be preprocessed by the laboratory system before being included in the input data set. Data values, such as concentrations or counts, may be normalized by a reference value (e.g., to account for different sampling techniques) or multiplied by a calibration factor (e.g., to account for different biological sample testing equipment). Data values may also be classified into different categories. The classification may have binary categories (e.g., present or not present; normal or abnormal) or have more than two categories (e.g., very low, low, normal, high, very high). The categories may be represented by a numerical value (e.g., present may equal 1 and not present may equal 0). As an example, age may be separated into categories of 0 to 17, 18 to 64, and 65 and over, with the categories represented numerically by "1", "2", and "3". In some embodiments, data values may be processed to produce an index value characterizing the data values. For example, medical history data may include the date, duration, and severity of various comorbidities. An index value (e.g., Charlson comorbidity index) may be calculated based on the medical history data to characterize the risk of the various comorbidities.

At block 120, the input data set is input into a machine-learning model to generate a score corresponding to a predicted degree to which the particular subject will tolerate a particular treatment. The particular treatment may include administration of rituximab, cyclophosphamide, doxorubicin hydrochloride, vincristine, and prednisolone (R-CHOP). In other embodiments, the particular treatment may include administration of cyclophosphamide, doxorubicin hydrochloride, or a combination thereof. Treatment may include M-CHOP (mosuntuzumab with CHOP) treatment. The machine-learning model may be stored in the model controller system.

The score generated by the machine-learning model may be a predicted probability of the particular subject tolerating the particular treatment. The probability may be weighted by the severity of adverse events. For example, the probability that death occurs may be multiplied by a factor to take into account the higher impact of death compared to other adverse events or a decrease in dose intensity.

The machine-learning model may include a set of parameters learned using multiple training data elements. Each of the multiple training data elements corresponds to a training subject. Each of the multiple training data elements includes a training input data set (e.g., including normalized data values, comorbidity indices, and data categories) and a label. The label indicates a tolerance of the training subject to the particular treatment. The tolerance may be a binary classification corresponding to "tolerated" and "not tolerated." In some embodiments, the label may indicate the severity of an adverse event suffered by the training subject. For example, a label of 1 may indicate death, a label of 0.5 may indicate hospitalization, and a label of 0 may indicate no adverse event. In some examples, the scale may be reversed to have labels indicate the level of tolerance. For examples, a label of 1 may indicate completing the treatment, and a label of 0 may indicate death.

The machine-learning model may include a function that relates received input data sets and the parameters to the score. The function may be generated by training the machine-learning model to predict the labels of the tolerances of training subjects with the training input data sets. The generated score for the particular subject may be the predicted tolerance of the particular subject to the particular treatment.

In some instances, the training input data sets includes a value for each of a set of variables, and the machine-learning model is configured to receive values for only a subset of the set of values as input to transform into a score. The subset may be identified by determining an extent to which each of the variables in the set of variables is predictive of tolerances. The determination may include performing a univariate analysis (e.g., for each of the variables in the set individually) or a multi-variate analysis (e.g., using some or all of the variables in the set). For example, a Pearson product-moment correlation may be evaluated between the variables and the tolerances. The variables with higher correlations may be identified as informative variables. In addition or alternatively, these informative variables may be analyzed to assess the value of each variable in predicting tolerance. The analysis may use transformations of variables or ranking algorithms (e.g., GameRank (Huang T K, Lin C J, Weng R C. Ranking individuals by group comparisons. Proceedings of the 23rd international conference on Machine learning. Pittsburgh, Pennsylvania, USA: Association for Computing Machinery; 2006:425-432), which his hereby incorporated by reference in its entirety for all purposes).

In some embodiments, the training input data set may include training subjects with a lower median age and/or fewer median comorbidities than subjects in the data set used for validation or used in practice. The median age of the training input data set may be 1 to 5, 5 to 10, 10 to 15, 15 to 20, or over 20 years less than the median age of the validation data set or the particular subject. The median age of the training input data set may be from 30 to 40, 40 to 50, 50 to 60, or 60 to 70 years old. The generated scores are therefore trained and developed in a younger, fit population and then validated or practiced on older populations. A younger population with fewer comorbidities may allow for better understanding of whether a subject tolerates a treatment by removing or reducing other known causes of hospitalization and death.

The machine-learning model may use the informative variables to determine different functions for predicting tolerances. A trial-and-error modeling process may be used to improve the performance or accuracy of the model. For example, the machine-learning model may dynamically adjust parameters and/or configurations based on cross-validated area under the curve (AUC) or bootstrap optimism metrics obtained as a result of previous iterations. Variable importance in these functions may be evaluated using a ranking algorithm. The performance of the functions in accurately predicting tolerances in a validation data set may be compared against each other. The function selected for the machine-learning model may be the model that most accurately predicts the tolerance or has a balance of accuracy and computational efficiency. The function may be limited to a certain number of variables (e.g., 1 to 5, 5 to 10, 10 to 15), which may be the most informative, most correlated, or top ranked variables.

The-machine learning model may include, for example, a regression model (e.g., a linear and/or logistic regression model), artificial neural network, decision tree, random forest model, support vector machine (SVM), naive Bayes classification, clustering algorithm, principal component analysis (PCA), singular value decomposition (SVD), t-distributed stochastic neighbor embedding (tSNE), as well as ensemble models that construct a set of classifiers and then classify new data points by taking a weighted vote of their predictions.

At block 130, a prediction of the tolerance of the particular subject to the particular treatment is output using the score. The prediction may be a non-numerical result. The prediction may be that the subject is not likely to tolerate the treatment. For example, the prediction may include that the subject is likely to suffer an adverse event such as death, illness requiring hospitalization, life-threatening event other than lymphoma, or persistent disability or incapacity. The prediction may also be that the subject is likely to tolerate the treatment. In some embodiments, the prediction may be a numerical result. The prediction may be a likelihood or probability of the particular subject tolerating the particular treatment. For example, if the score is a probability of the tolerance of the particular subject, the prediction may be equal to the score. In some embodiments, the score may be a binary classification of whether a particular subject is likely to tolerate the particular treatment, and outputting the prediction corresponding to the binary classification. The prediction is not a prediction of the effectiveness of the treatment against lymphoma. The prediction may be output and sent to the care provider system.

Determining the prediction may involve the machine-learning model or post-processing technique comparing the score to a cutoff value. The cutoff value may be determined using scores determined by the machine-learning model for multiple reference subjects. For example, a subset of the multiple reference subjects may be identified, where the score of each reference subject in the subset is lower than a score of each reference subject not in the subset. The size of the subset may correspond to a predefined percentage relative to a size of the multiple reference subjects. The cutoff value may be defined as a given value that separates scores of the reference subjects in the subset from scores of reference subjects not in the subset. In this manner, the cutoff value may correspond to a percentile of the reference subjects having the lowest scores. For example, the cutoff value may correspond to the lowest 5%, 10%, 15%, 20%, 25%, 30%, 40%, 50%, 60%, 70%, 75%, 80%, 90%, or 95% of the scores from the reference subjects. If upon determining that the particular subject is in the subset of reference subjects having the lowest scores, the prediction may be that the particular subject is not likely to tolerate the particular treatment. If the particular subject is not in the subset of reference subjects having the lowest scores, the prediction may be that the particular subject is likely to tolerate the particular treatment.

The cutoff value may be determined with a classifier that uses a loss function that prioritizes distinguishing subjects who do (or do not) tolerate the treatment. For example, the cutoff value may be determined to avoid false negatives or false positives. The machine-learning model may use a clustering model, (e.g., PCA or Independent Component Analysis [ICA]) to determine a boundary separating clusters. The clusters may represent different degrees of tolerance (e.g., death, hospitalization, dose intensity reduction). The cutoff value may represent a line, plane, or hyperplane between clusters. Comparing the score to the cutoff value may include calculating a tolerance metric from the score and other components identified by the clustering model and then comparing the tolerance metric to the cutoff value.

Comparing the score to the cutoff value may include determining that the score exceeds the cutoff value. Based on the comparison of the score exceeding the cutoff value, the machine-learning model (or post-processing analysis by the care provider system) may determine the particular subject is in or is likely in a particular subset of subjects having similar tolerances (e.g., a subset with subjects that tolerate the treatment, a subset with subjects that do not tolerate the treatment but also do not die from the treatment). The machine-learning model may then output the prediction of the tolerance of the particular subject to the particular treatment by using the characteristic of the subset. For example, if the particular subject is in a subset with subjects that do not die from the particular treatment, the outputted prediction may be that the particular subject is not likely to die from the particular treatment. In some embodiments, the score for the particular subject may not exceed the cutoff value, indicating or suggesting that the particular subject does belong to a particular subset.

Cutoff values may be selected to achieve a predefined accuracy. For example, the cutoff values may be determined to achieve a predefined level of sensitivity or a predefined level of specificity for predicting whether a subject tolerates the particular treatment in the multiple reference subjects. The predefined level of sensitivity or specificity may each independently be 60% to 70%, 70% to 80%, 80% to 90%, or 90% to 95%. The cutoff value may be selected to achieve a predefined area under the curve (AUC) in a receiver operating characteristic (ROC) curve. The predefined AUC may be 0.6 to 0.7, 0.7 to 0.8, 0.8 to 0.9, or 0.9 to 0.95.

The prediction of the tolerance may be determined solely using the score. In some instances, the prediction may use different prognostic indicators in addition to the score. For example, the prediction may use an average of different prognostic indicators, including the International Prognostic Index (IPI), ECOG PS (Eastern Cooperative Oncology Group Performance Status), age, or a geriatric assessment.

In response to a prediction that the particular subject will not tolerate or is unlikely to tolerate the particular treatment, a recommendation that the particular subject be enrolled in a clinical study may be output. The enrollment of the particular subject may be by a medical practitioner or by a treatment device, which may be any treatment device described herein. A recommendation that a medical practitioner not administer the particular treatment to the particular subject may be outputted. The recommendation may include administering the particular treatment at a lower dose. The medical practitioner may be recommended to administer an alternative treatment, such as a different drug combination, radiation therapy, a bone marrow transplant, or palliative care. Recommendations may be sent to the care provider system, which may then output the recommendations. Process 100 may include administering the alternative treatment by a treatment device or by a medical professional.

On the other hand, if the prediction is that the particular subject will tolerate or is likely to tolerate the particular treatment, a recommendation may be output to administer the particular treatment to the particular subject. The particular treatment may be administered to the particular subject.

Process 100 may be repeated one or more times after the particular subject starts particular treatment. The generated score may be monitored over time. If the score shows a change from a previous score, the particular treatment for the particular subject may be paused or ended. The change may be a change in the score that results in a different outputted prediction. In some embodiments, the change may be a statistically significant change (e.g., over 1, 2, or 3 standard deviations based on scores from reference subjects).

It will be appreciated that, in alternative embodiments, the input data set may include raw data from an assay, and the model controller system may pre-process (e.g., normalize or categorize) the raw data. Additionally, the score generated by the machine-learning model may be compared to the cutoff value in a post-processing step performed by the care provider system. Furthermore, outputs and recommendations by model controller system 320 may be displayed or generated by the care provider system.

III.A. Training Methods

Figure 2:
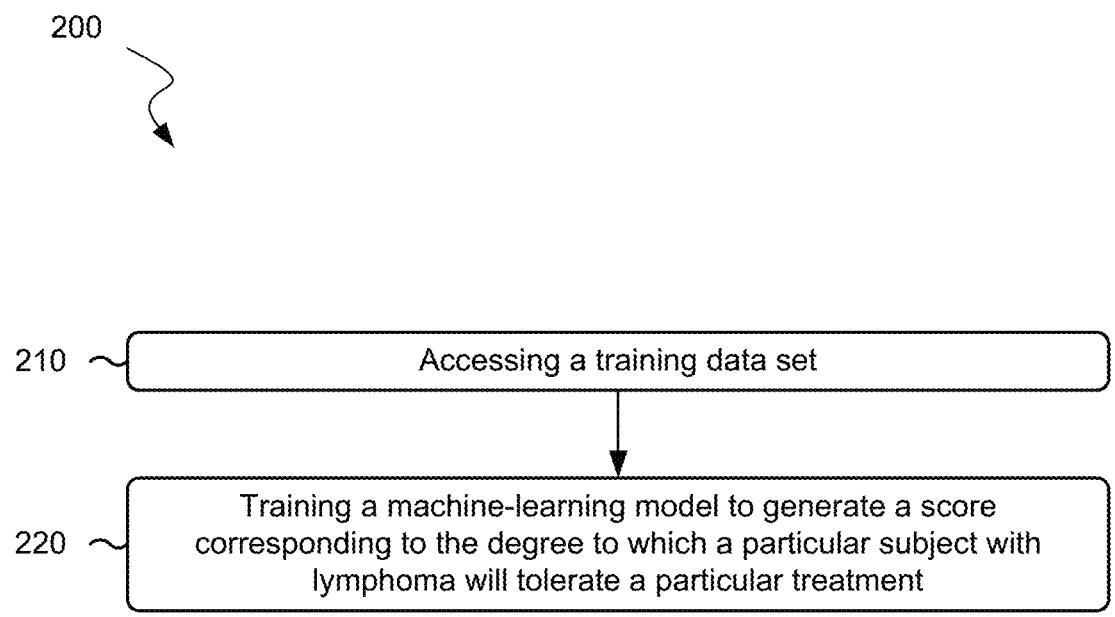
FIG. 2 is a process for training a machine-learning model according to some embodiments of the present disclosure.

Some embodiments may include a computer-implemented method for training a machine-learning model. FIG. 2 shows a process 200 for training a model (e.g., a machine-learning model used at block 120 of process 100).

At block 210, a training data set is accessed. The training data set includes multiple training data elements. Each of the multiple training data elements correspond to a training subject with lymphoma. Each of the multiple training data elements include a training input data set and a label. The label indicates a tolerance of the training subject to a particular treatment. The label may be any label described herein. For example, the label may be a binary indication (e.g., yes or no) of whether a subject tolerated the particular treatment. In other examples, the label may reflect different severities of cases where the subject has not tolerated the particular treatment. The training subjects may include subjects that tolerated the particular treatment and subjects that did not tolerate the particular treatment (e.g., suffered an adverse event). In some embodiments, the training subjects may be at least 60, 65, 70, 75, 80, or 85 years old. The training data set may have the values described for the input data set in process 100 of FIG. 1.

At block 220, a machine-learning model is trained to generate a score corresponding to the degree to which a particular subject with lymphoma will tolerate the particular treatment. The training uses the training data set. Training the machine-learning model includes learning a set of parameters. The set of parameters may include any parameters disclosed herein. Training the machine-learning model also includes determining a function relating the set of parameters to a predicted tolerability.

Machine-learning algorithms or deep learning algorithms could be used for training, including but not limited to support vector machines (SVM), decision tree, naive Bayes classification, logistic regression, clustering algorithm, principal component analysis (PCA), singular value decomposition (SVD), t-distributed stochastic neighbor embedding (tSNE), artificial neural network, as well as ensemble methods which construct a set of classifiers and then classify new data points by taking a weighted vote of their predictions.

The function relating the set of parameters to the predicted tolerability may include any formula described herein. The parameter may include an input data value and a coefficient and/or an operator (e.g., log, square root, raised to a power). The function may be a linear combination or non-linear combination of parameters.

Examples of using the GOYA data set for training machine-learning models are described below.

III.B. Example System

Figure 3:
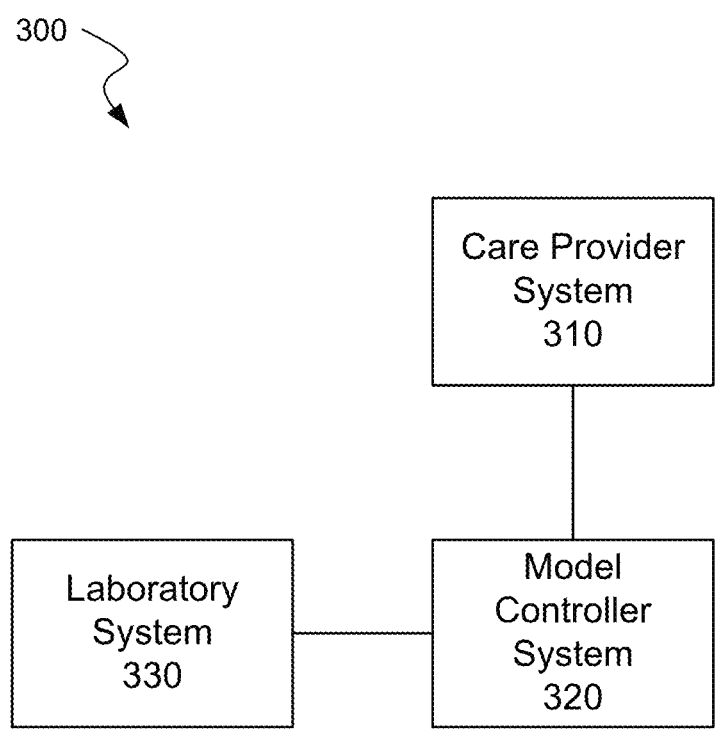
FIG. 3 is a computer network for using a machine-learning model to predict tolerability of a particular treatment in a particular subject according to some embodiments of the present disclosure.

FIG. 3 shows a system 300 that may be used to implement methods or steps of process 100. System 300 includes care provider system 310. Care provider system 310 may include a computer system and be operated by a health care provider, including a clinic, a hospital, or a medical practitioner. The health care provider operating care provider system 310 may be responsible for treatment of lymphoma in the particular subject of process 100 of FIG. 1. The health care provider may identify the particular subject as a possible recipient of a particular treatment. The health care provider may input information regarding the particular subject and the particular treatment into care provider system 310. For example, the name of the particular subject and the type of particular treatment (e.g., R-CHOP or any treatment described herein) may be input into care provider system 310.

Care provider system 310 may send a request to model controller system 320 to provide a prediction of the tolerance of the particular subject to the particular treatment. Model controller system 320 may include a computer system. Model controller system 320 may include a non-transitory computer readable storage medium, which stores the machine-learning model and includes instructions to perform the steps of process 100. Model controller system 320 may access an input data set that includes multiple input data values, each input data value corresponding to a variable of a set of variables, as in block 110. The input data set may be stored in model controller system 320.

Model controller system 320 may send a request to a laboratory system 330 to access the input data values. Laboratory system 330 may include multiple laboratory devices. These laboratory devices may perform assays (e.g., blood panel) on biological samples from the particular subject. The data from these assays may be stored on a data storage device in laboratory system 330. Laboratory system 330 may send the input data values to model controller system 320.

The input data set may be inputted into the machine-learning model of model controller system 320, as in block 120 of process 100. Model controller system 320 may search for the values of specific variables in the input data set and then insert the values into the appropriate memory locations of the machine-learning model. The machine-learning model may be the machine-learning model described in process 100 of FIG. 1 and trained in process 200 of FIG. 2.

Model controller system 320 may then run the machine-learning model to generate a score corresponding to the degree to which the particular subject will tolerate a particular treatment. The score may be generated as in block 120 of process 100.

The generated score may be used to determine a prediction of the tolerance of the particular subject to the particular treatment, as in block 130 of process 100. The prediction may be sent from model controller system 320 to care provider system 310. Care provider system 310 may display the prediction or may communicate the prediction to a medical practitioner. In some embodiments, care provider system 310 may determine the prediction of the tolerance using the generated score.

Care provider system 310 may determine recommendations based on the prediction of the tolerance and output the recommendations. The recommendations may be the recommendations described in process 100. The recommendations may be displayed or communicated to the medical practitioner, who may follow the recommendations. In some embodiments, the recommendations may be determined by model controller system 320 and sent to care provider system 310.

It will be appreciated that, in alternative embodiments, care provider system 310 and model controller system 320 may share components. For example, instructions associated with care provider system 310 may occupy a portion of a data store, while instructions associated with model controller system 320 may occupy another portion of the same data store.

III.C. Example Computer System

Figure 4:
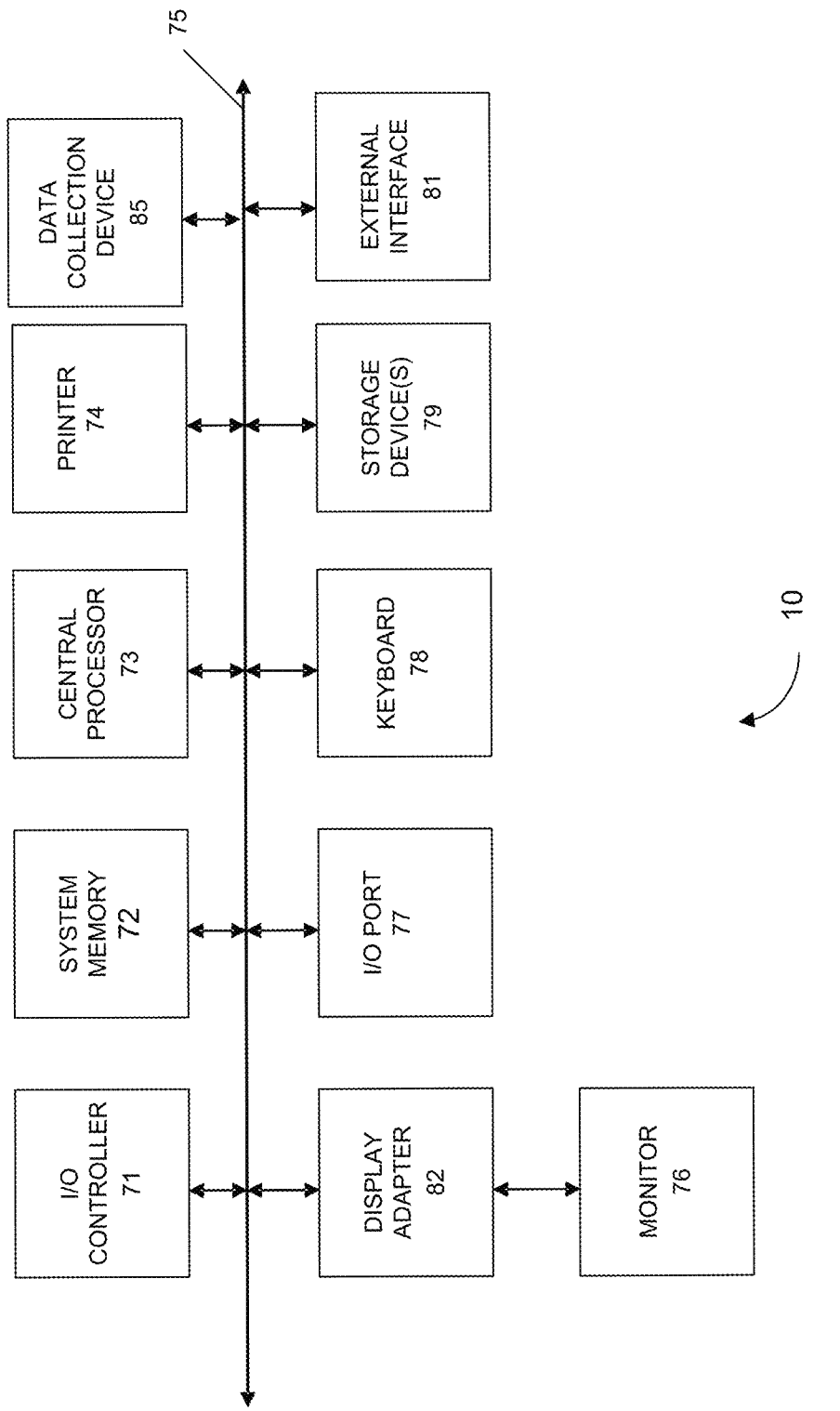
FIG. 4 is a computer system according to some embodiments of the present disclosure.

Any of the computer systems mentioned herein, including computer systems for the care provider system 310, model controller system 320, and laboratory system 330, may utilize any suitable number of subsystems. Examples of such subsystems are shown in FIG. 4 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 4 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, Lightning). For example, I/O port 77 or external interface 81 (e.g. Ethernet, Wi-Fi, etc.) can be used to connect computer system 1500 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. System memory 72 and/or storage device(s) 79 may store the input data set, machine-learning model, set of parameters, function, and results generated from the model. Another subsystem is a data collection device 85, such as a camera, microphone, accelerometer, and the like. Any of the data mentioned herein can be output from one component to another component, can be output from one computer system to another computer system, and can be output to the user. Data can be output to the user through monitor 76.

A computer system can include several of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of some embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement some embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for outputting any of the results mentioned herein to a user (e.g., a medical practitioner).

Any of the methods described herein may be totally or partially performed with a computer system including one or more processors, which can be configured to perform the steps. Thus, some embodiments can be directed to computer systems configured to perform the steps of any of the methods described herein, potentially with different components performing a respective step or a respective group of steps. Although presented as numbered steps, steps of methods herein can be performed at a same time or at different times or in a different order that is logically possible. Additionally, portions of these steps may be used with portions of other steps from other methods. Also, all or portions of a step may be optional. Additionally, any of the steps of any of the methods can be performed with modules, units, circuits, or other means of a system for performing these steps.

IV. Examples

Subjects from the GOYA (Vitolo U, Trněný M, Belada D, et al. Obinutuzumab or rituximab plus cyclophosphamide, doxorubicin, vincristine, and prednisone in previously untreated diffuse large B-cell lymphoma. *J Clin Oncol.* 2017; 35(31):3529-3537) and MAIN (Seymour J F, Pfreundschuh M, Trneny M, et al. R-CHOP with or without bevacizumab in patients with previously untreated diffuse large B-cell lymphoma: final MAIN study outcomes. *Haematologica.* 2014; 99(8):1343-1349) trials were studied to delineate factors associated with poor R-CHOP tolerability in subjects with DLBCL. The aim was to develop a model (TRAIL; Tolerability of R-CHOP in Aggressive Lymphoma) to predict the risk of intolerability to R-CHOP induction therapy using variables captured at baseline, and validate it using data from GOYA and from subjects receiving 21-day cycles of R-CHOP in the external independent MAIN study.

For the purpose of this analysis, the composite tolerability endpoint (intolerability to CHOP) was defined as the occurrence of at least one of the following events within the first 6 cycles: adverse event (AE) leading to withdrawal of cyclophosphamide and/or doxorubicin before completion of 6 cycles, death without disease progression (PD), or average dose intensity of cyclophosphamide and doxorubicin <80% not related to PD. The rationale for choosing an endpoint based on these components is that it identifies those subjects not receiving an optimal dose intensity of CHOP chemotherapy due to poor tolerability.

IV.A. Model Development with GOYA Dataset

Data for model development was obtained from the multicenter, open-label, randomized phase III GOYA trial (NCT01287741). Subjects with DLBCL were recruited from 207 centers in 29 countries between July 2011 and June 2014. Eligible subjects were aged 18 years or older, previously untreated and diagnosed with CD20-positive DLBCL. Other inclusion criteria included the following: an Eastern Cooperative Oncology Group performance status (ECOG-PS) of 0 to 2; adequate hematologic, liver, and kidney function; left ventricular ejection fraction of ≥50% and no significant, uncontrolled concomitant diseases. Subjects in GOYA were treated with either 6 or 8 21-day cycles of R-CHOP or obinutuzumab plus CHOP (G-CHOP). Median follow-up at the time of the final analysis (January 2018) was 48 months. Since there was no statistical difference in outcome detected between the obinutuzumab and rituximab treatment arms in GOYA, the data from both arms were pooled for this analysis.

Figure 5:
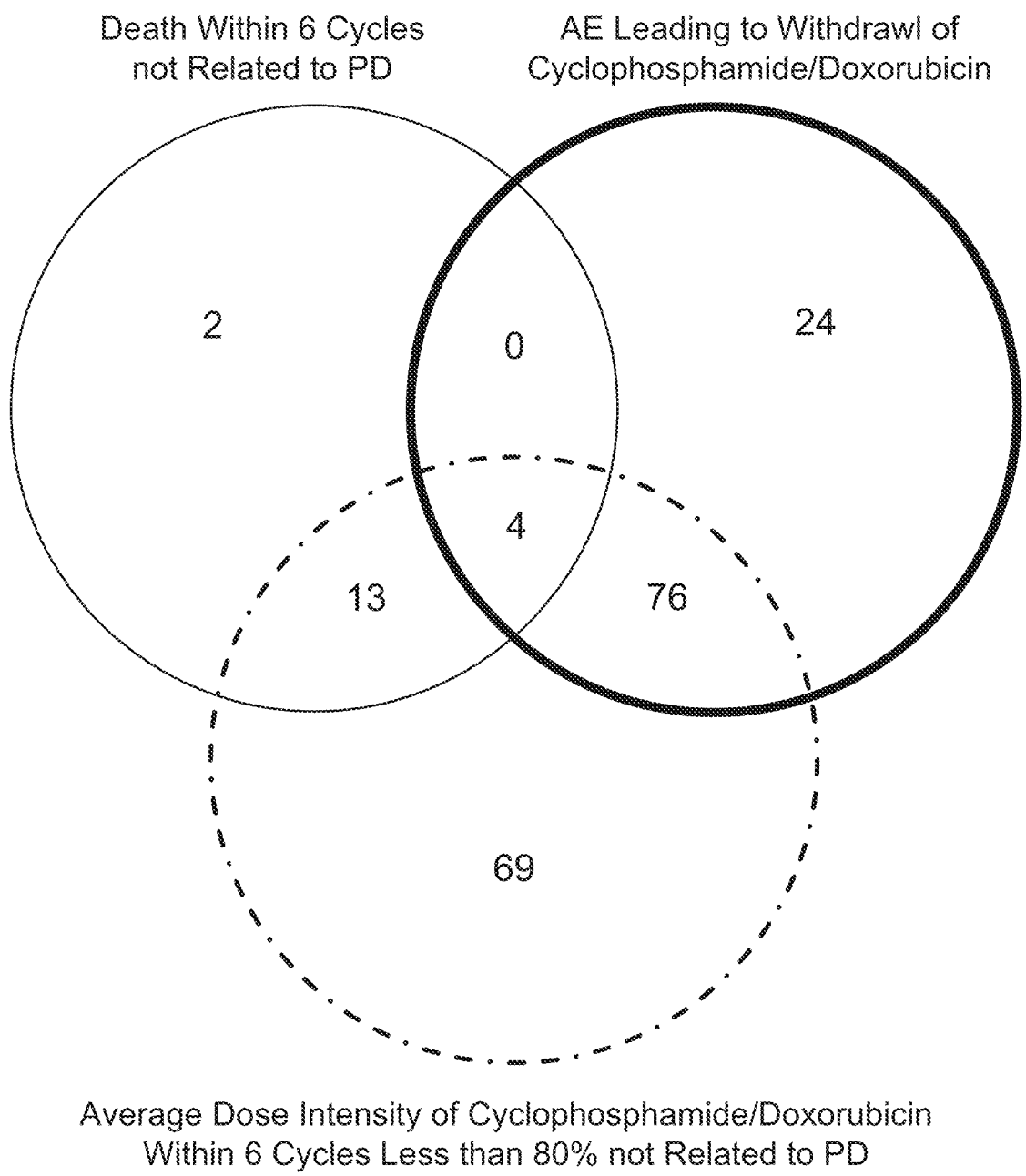
FIG. 5 is a Venn diagram of the hybrid tolerability endpoint according to some embodiments of the present disclosure.
Figure 6:
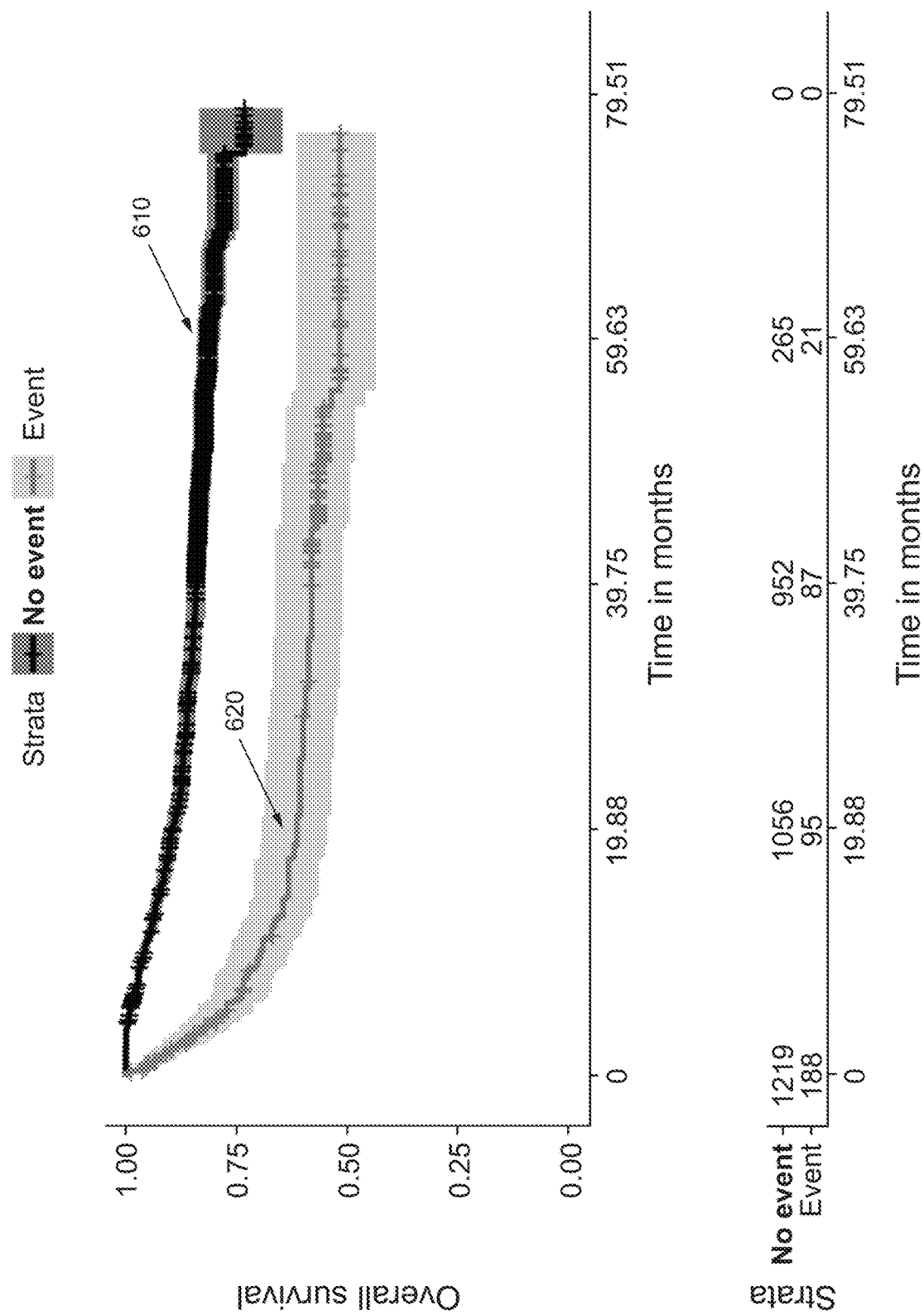
FIG. 6 is a graph of the overall survival against time in months for those with events and without events according to some embodiments of the present invention.

Of 1,407 evaluable subjects that initiated anti-CD20+ CHOP, the hybrid tolerability binary endpoint occurred in 188 (13.4%) (FIG. 5). There were 104 (7.4%) subjects with adverse events (AEs) leading to withdrawal of cyclophosphamide and/or doxorubicin; 162 (11.5%) instances of reduced average relative dose intensity of cyclophosphamide and doxorubicin <80% intended; and 19 (1.4%)

deaths within the first 6 cycles not related to progressive disease (PD). FIG. 6 shows a plot of the overall survival against time in months for those with events and without events. The x-axis shows the time in months. The y-axis shows the overall survival rate. The top line (line 610) of the plot is subjects with no adverse events. The bottom line (line 620) of the plot is subjects having an adverse event. FIG. 6 shows that those suffering adverse events have a lower overall survival rate.

Statistical modeling was performed retrospectively using data from the GOYA safety evaluable population (n=1407). The GOYA data was divided into a 75% training set (n=1051), used for model training and cross-validation, and a 25% holdout set (n=356) that was blinded to the analysis team to serve as a test set for validation. The training set was divided into four folds for cross-validation, each including between 260 and 265 subjects. These four folds and the holdout set were created in a way to achieve a balanced distribution of the following variables: immunotherapy group, International Prognostic Index (IPI) category, PFS event, and sum of product diameters of lymphoma lesions. Further details of the balanced 4-fold cross-validation generation are found in the supplemental methods. Random 10-fold cross-validation and bootstrapping using the GOYA training data were additionally used to assess model performance.

Model development included the following tasks: evaluation of correlation between individual predictor variables and outcome, examination of predictor distributions, creation of transformed predictors if indicated, and finally a series of model evaluation stages. The steps prior to model validation were performed on only the GOYA training data and not the holdout data.

III.A.1. Predictor Screening

The associations between candidate covariates and the composite endpoint were initially investigated to identify highly prognostic predictors as well as to attempt to construct informative variables. Pearson product-moment correlations (with 95% CI and p values) were evaluated between each predictor and the composite endpoint. The correlations between predictors and the individual components of the composite endpoint were used for the predictor selection and correlations between each pair of individual predictors were also evaluated.

III.A.2. Predictor Construction

As a consequence of the correlation analysis, univariate predictor distributions were further analyzed to construct informative variables. Distributions of candidate predictor variables were examined, and a variety of transformations were considered, e.g., categorizing continuous variables, evaluating non-linear transformations (square root, log, Box-Cox). To assess the predictive value of each predictor variable, the ranking algorithm, GameRank (Huang T K, Lin C J, Weng R C. Ranking individuals by group comparisons. Proceedings of the 23rd international conference on Machine learning. Pittsburgh, Pennsylvania, USA: Association for Computing Machinery; 2006:425-432) was implemented.

III.A.3. Determining the TRAIL Model

Determination of the final model for prediction was an iterative process. Starting with a set of initial models based on highly correlated predictors, a trial-and-error modelling process was followed to improve the cross-validated area under the curve (AUC) and the bootstrap optimism. Bootstrapped estimates for model generalization error and optimism were obtained using the 0.632 method. AUCs of folds were combined as a weighted average to obtain a pooled estimate. Variable importance was determined using GameRank and their included predictors were compared based on the AUC of the Receiver Operating Characteristic (ROC). After the model was selected, the contribution of each predictor was evaluated and the availability of predictors in the clinical setting was also considered for predictor selection.

A model was identified to receive, as input: albumin level, percentage of bone marrow lymphocytes, Charlson comorbidity index (CCI), creatinine clearance, and previous history of heart, vascular or diabetes comorbidities (FIG. 7). "Events" refers to an adverse event, and the R-CHOP treatment is not tolerated. "Total events" refers to all events, including those situations where the R-CHOP treatment is tolerated. "Odds ratio" refers to an increase in the odds of having an adverse event as a result of a certain classification of a variable. For example, with cardiovascular/diabetes medical history, under the presence of the medical history, the odds of an adverse event versus not having an adverse event are $$\frac{39}{194-39} = 0.252.$$

Under the absence of such a medical history, the odds of an adverse event versus not having an adverse event are $$\frac{95}{857-95} = 0.125.$$

The odds ratio is 0.252/0.125=2.02, which means that having a cardiovascular/diabetes medical history shows an 2.02 times greater likelihood of an adverse event. The 95% confidence limits are shown in parentheses in the column. LLN in FIG. 7 stands for lower limit of normal. The Tolerability of R-CHOP In Aggressive non-Hodgkin Lymphoma (TRAIL) model was trained on 742 subjects with complete data. FIG. 7 shows that more total events with higher albumin, creatinine clearance, CCI, and the absence of cardiovascular/diabetes medical history.

Figure 8:
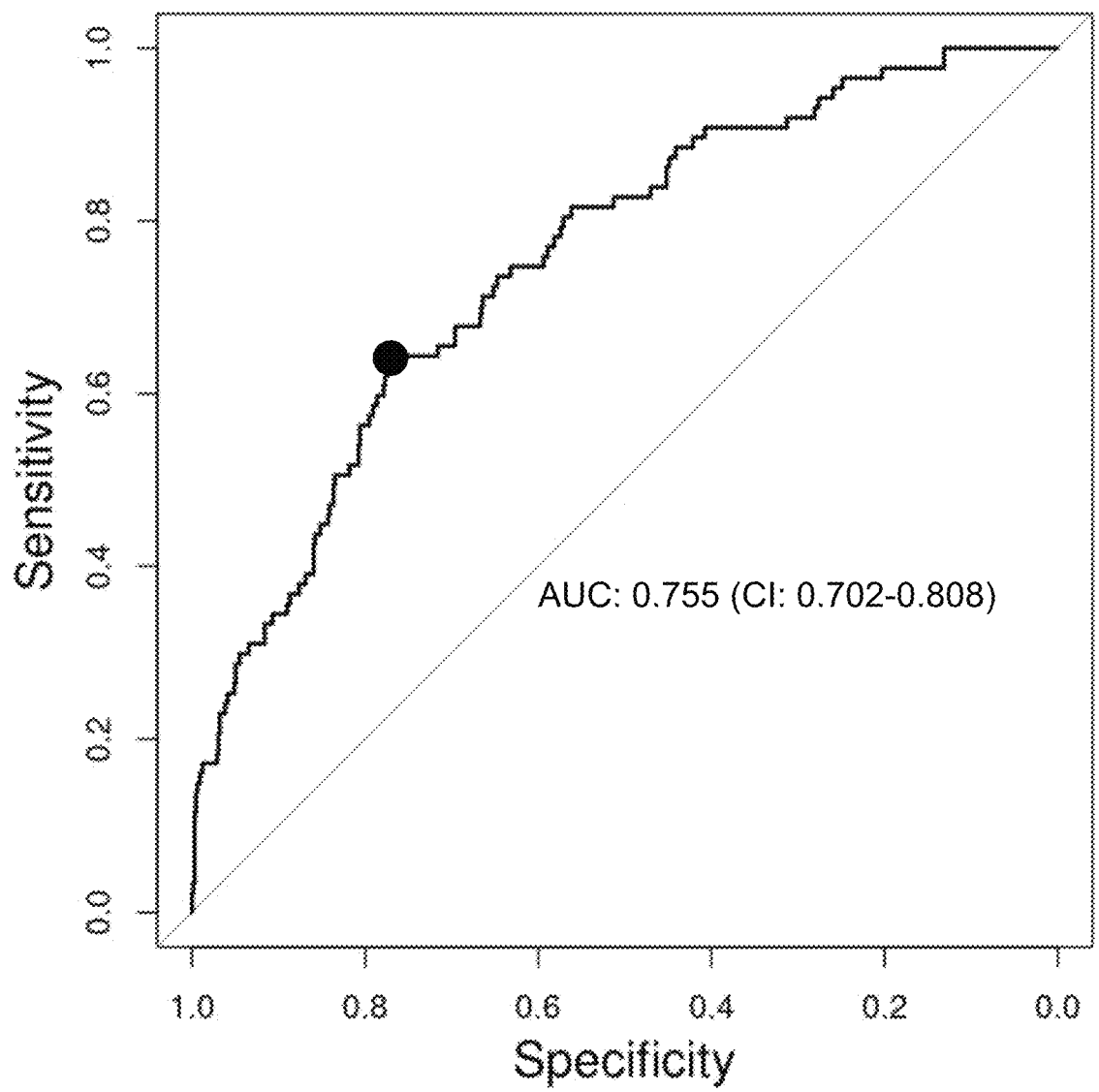
FIG. 8 shows a receiver operating characteristic (ROC) curve for the Tolerability of R-CHOP In Aggressive non-Hodgkin Lymphoma (TRAIL) algorithm according to some embodiments of the present disclosure, the highlighted point representing one possible set point for the TRAIL model that trades off between sensitivity and specificity.

An area under the receiver operating characteristic curve (AUC) of 75.5% was achieved, as was a cross validation (CV) AUC of 74.9% (sensitivity=75%, specificity=69.6%) (FIG. 8). CI in FIG. 8 stands for confidence interval. To create a simpler model using information available in the routine clinical setting, bone marrow lymphocyte levels was removed from the set of input variables, and a model was trained on 1022 subjects with complete data. A CV AUC of 70.1% (sensitivity=68.1%, specificity=67.2%) was achieved. Other top ranking models with complete data on all subjects achieved AUCs >70% and included age, hemoglobin, T-cell counts, proportion of TH cells, and lactate dehydrogenase (LDH). Implementations of CCI alone performed less well with a CV AUC of 62.9%.

One example TRAIL model found is of the form of equation (1):

HYBRID.OUTCOME~$I$(NOIMP.CRCL^-1)+log (NOIMP.ALBUM)+CHARLSON+ JUN20.HVD+sqrt(NOIMP.BMLYMP)+log(NO-IMP.CRCLBSA)     (1)

Equation (1) does not list the coefficients before each term. The coefficients can be determined through a logistic regression or other fitting algorithms. In other words, a term such as CHARLSON is multiplied by a coefficient in the model. The operator I is inverse. NOIMP refers to no imputation (i.e., estimation of values when missing). JUN20 refers to the date on which the data was acquired. The model need not be limited to only one date for acquiring data.

The output of the model (e.g., HYBRID.OUTCOME) may be a score. The score may be compared to a threshold. The threshold may be determined from one or more reference subjects known to tolerate or known not to tolerate a treatment (e.g., R-CHOP) for DLBCL or other lymphomas. A score exceeding the threshold may indicate that it is predicted that a subject will not tolerate a treatment or has greater than a certain probability (e.g., 30%, 40%, 50%, 60%, 70%, 80%, or 90%) of suffering an adverse event as a result of the treatment.

Figure 9:
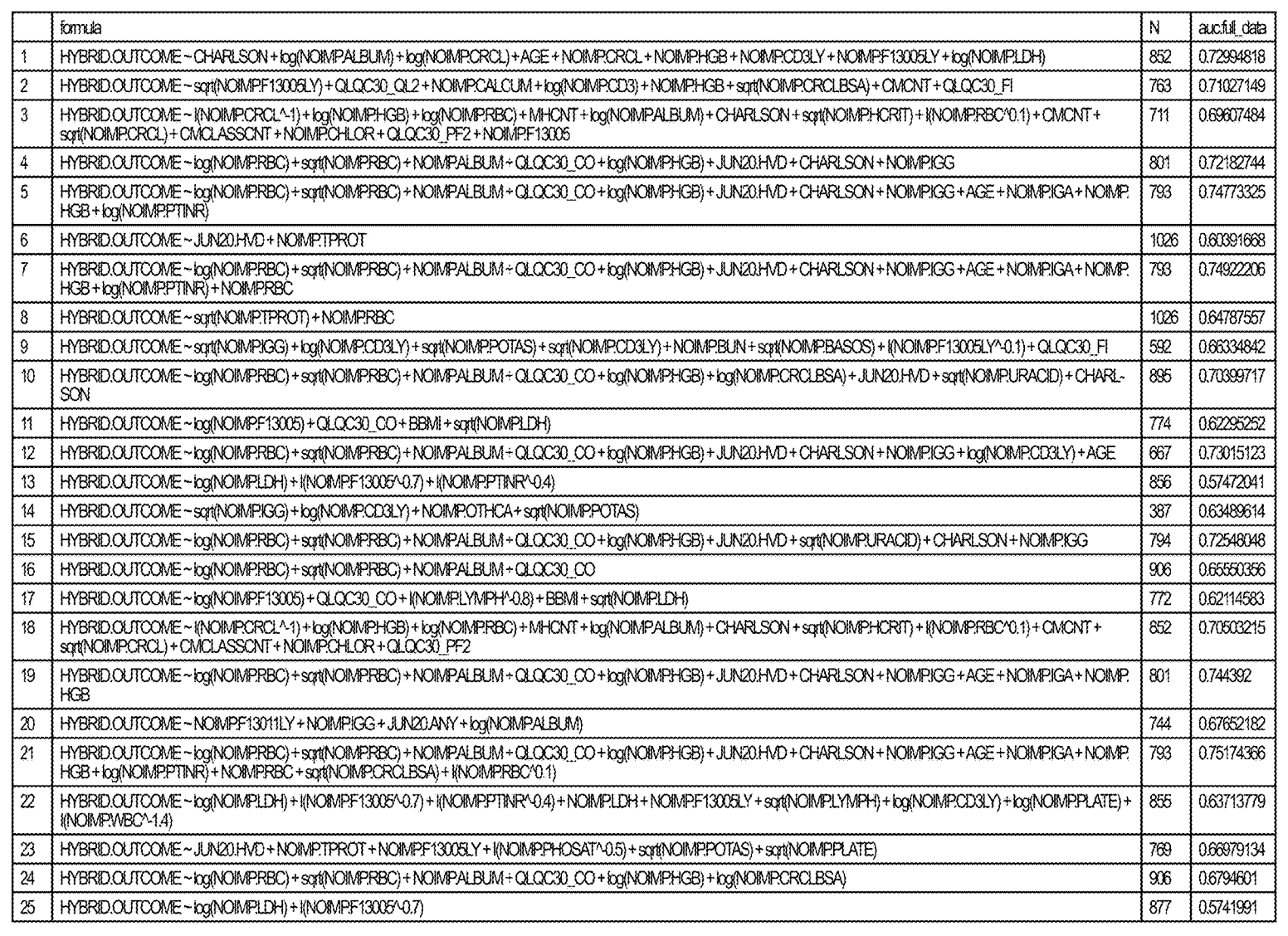
Figure 9:
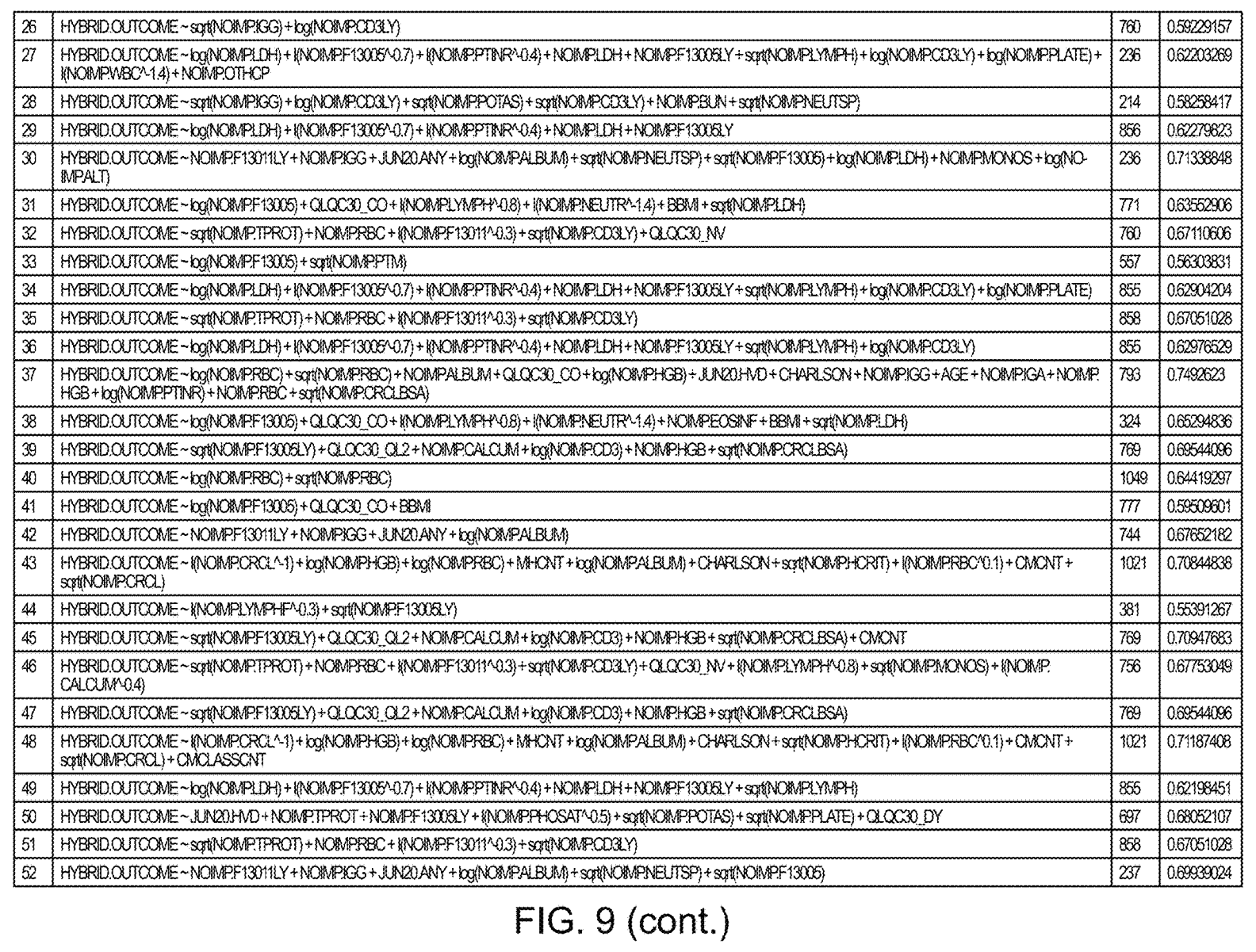
Figure 9:
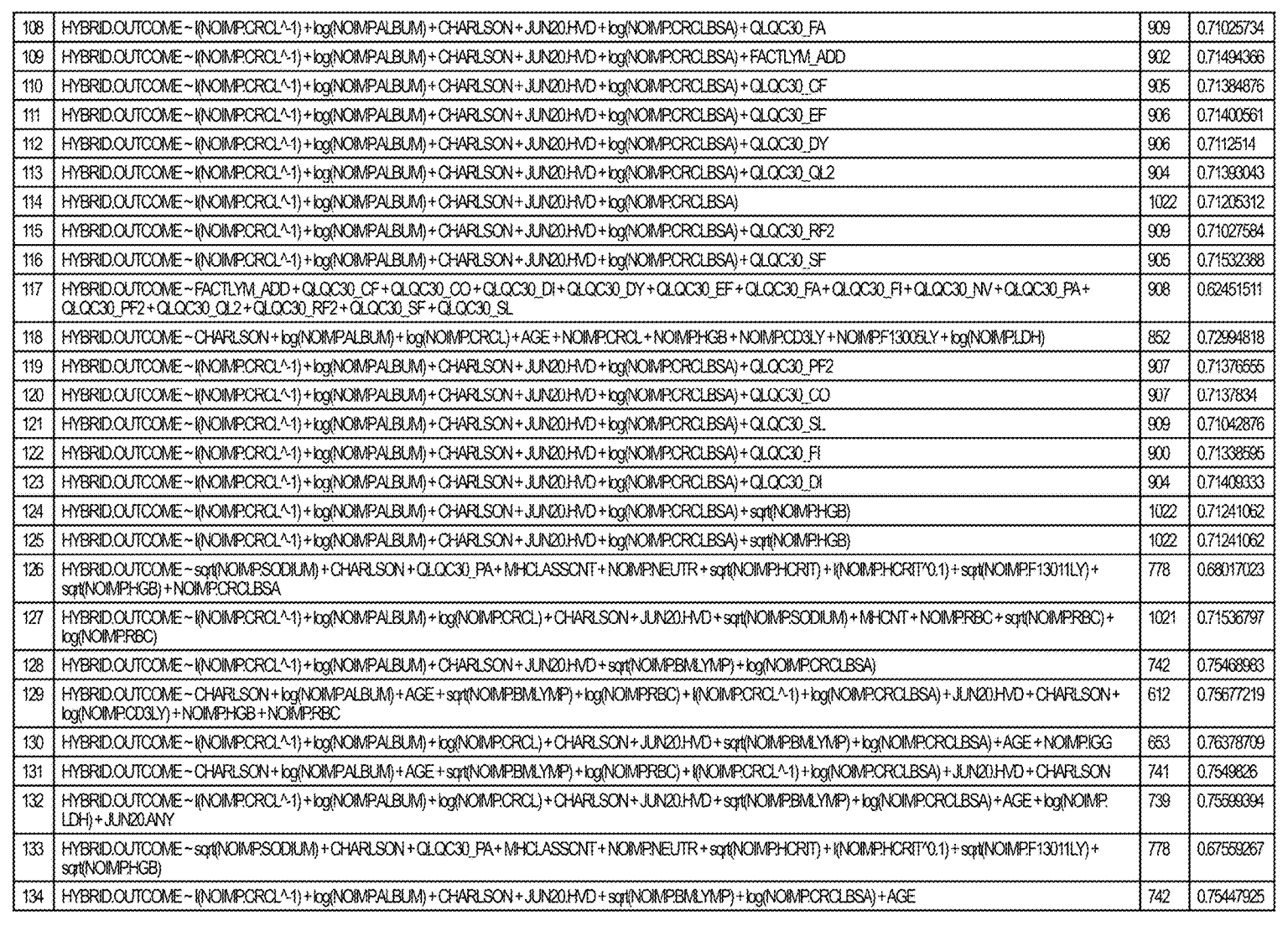
Figure 9:
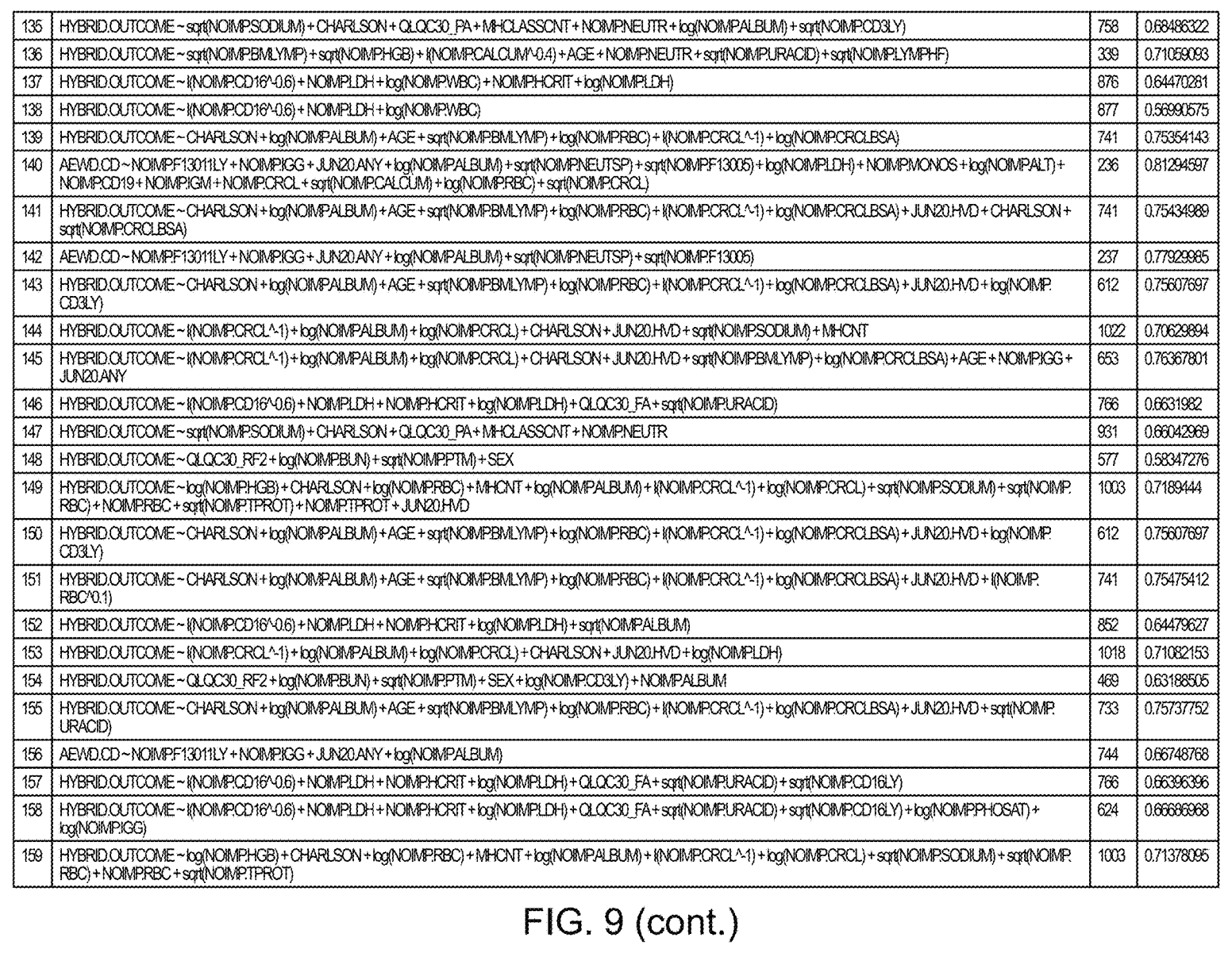
Figure 9:
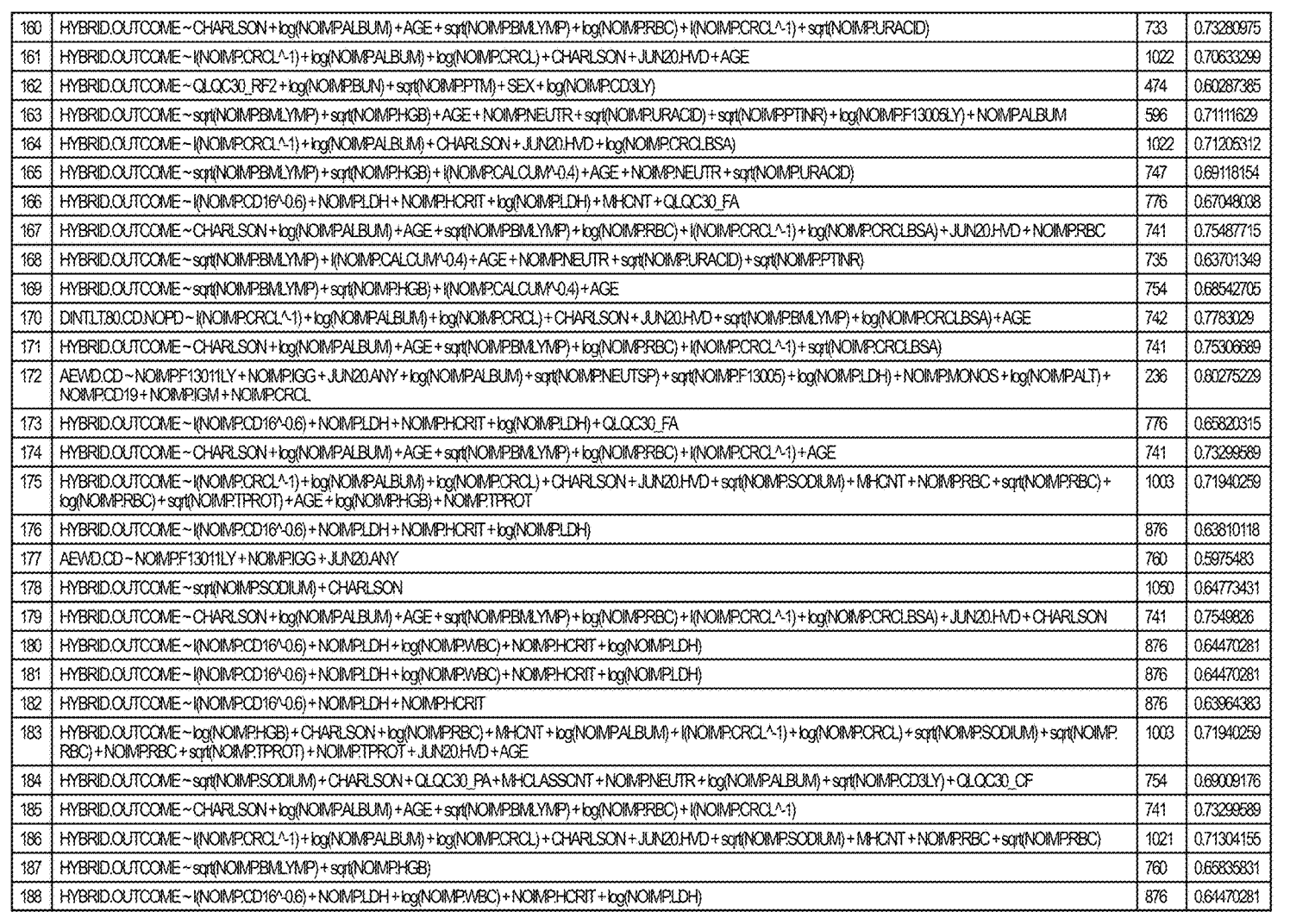
Figure 9:
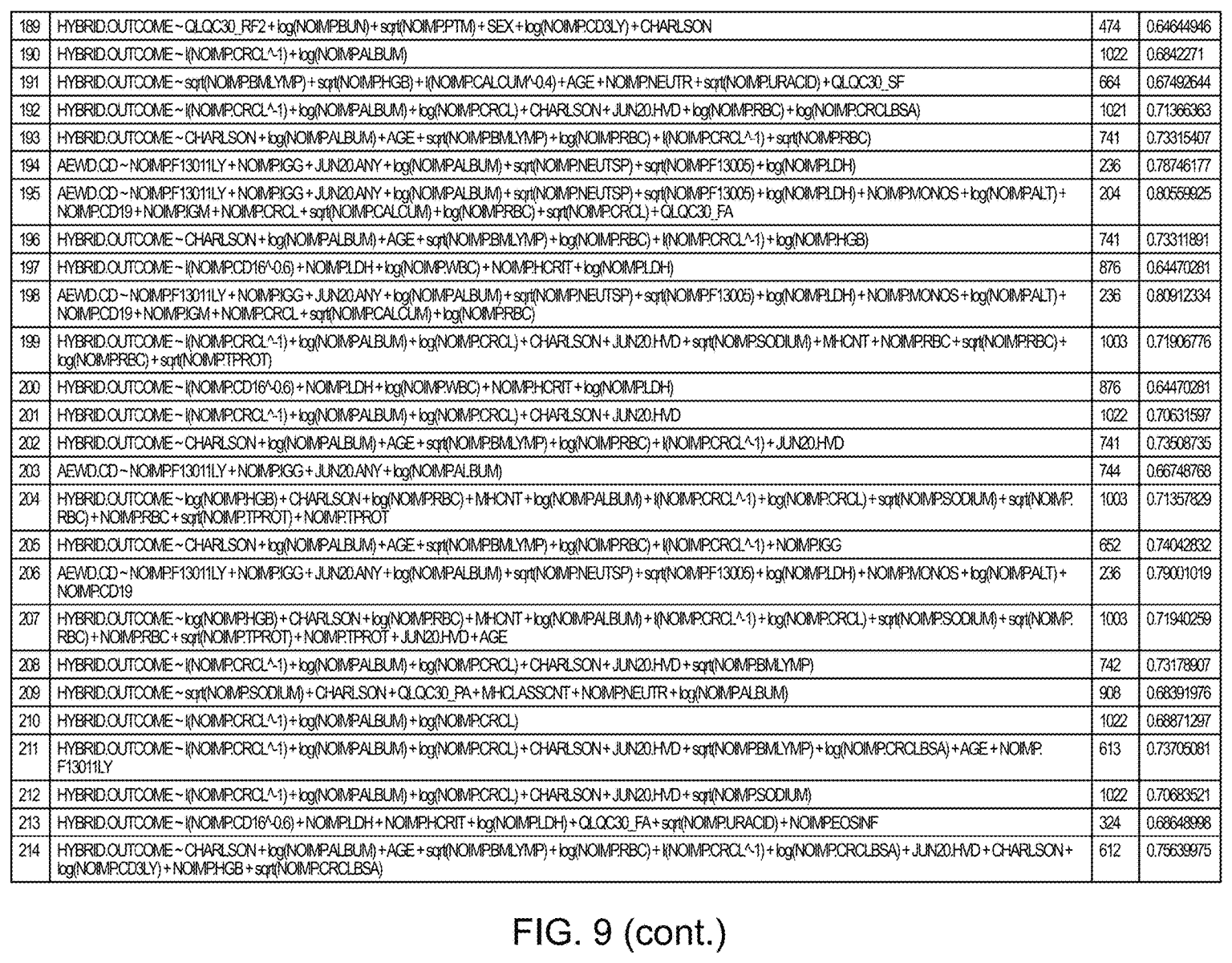
Figure 9:
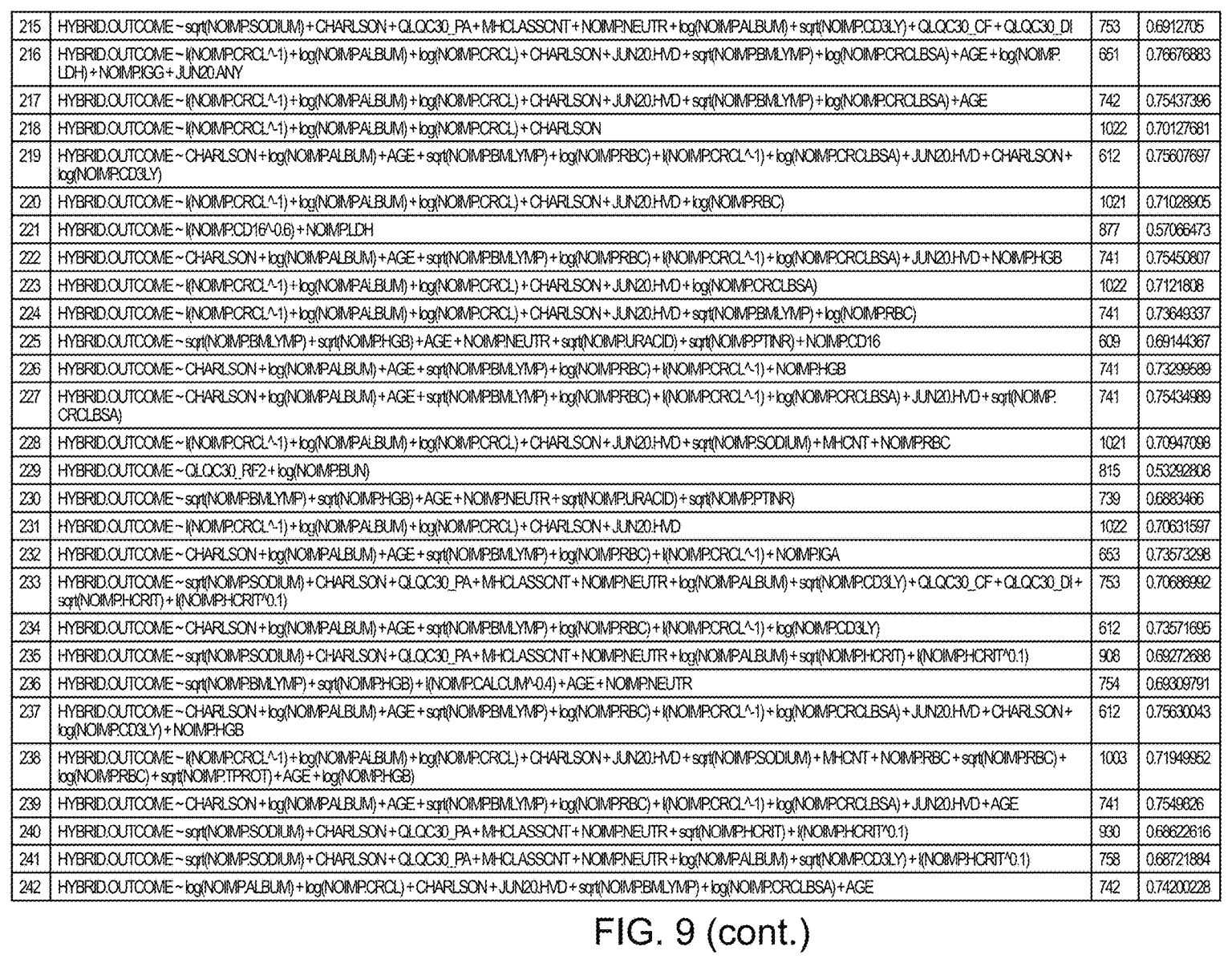
Figure 9:
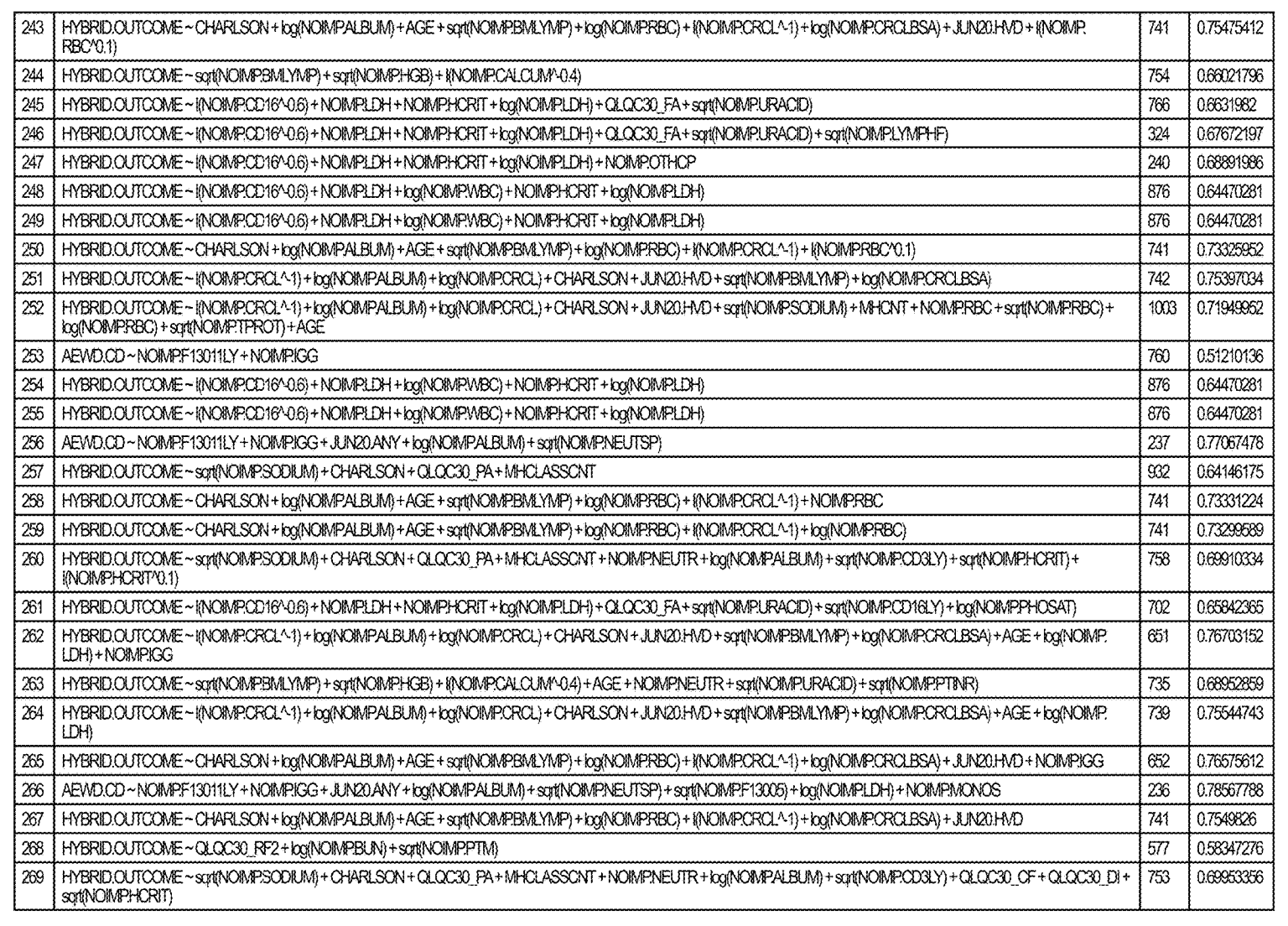
Figure 9:
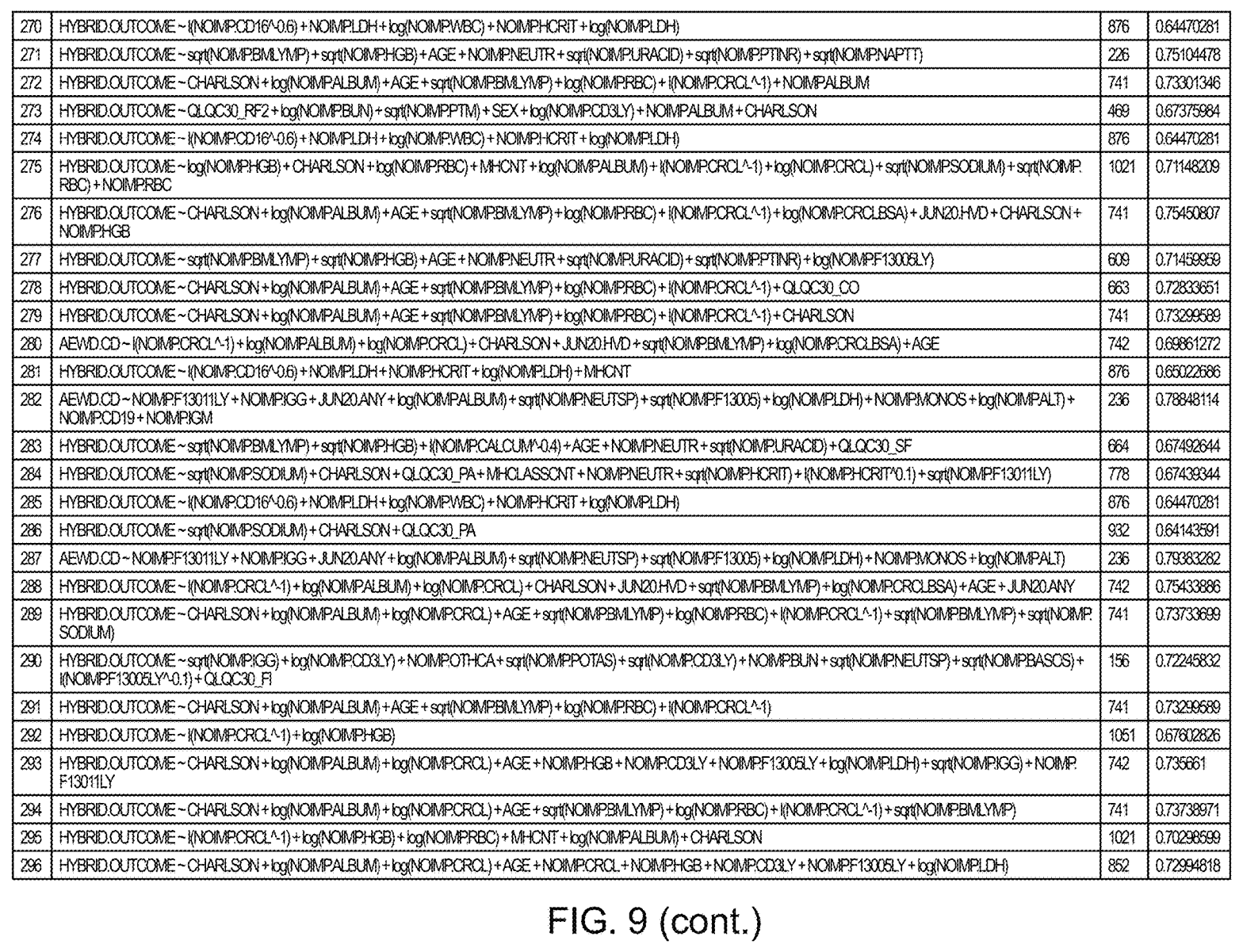

The model shown in equation (1) and represented by the table in FIG. 1 is not the only model that may be used to determine negative susceptibility to treatments for DLBCL or other lymphomas. FIG. 9 lists other models as formulas without coefficients that may determine negative susceptibility to treatments and the AUCs for each model. Terms used in FIG. 9 are listed in Table 5. The label auc.full_data refers to the AUC as calculated and fit on the full training data. Any of these formulas in FIG. 9 may be the function used with the machine-learning model of block 120. A model is not limited to the four-variable example model in equation (1).

Models where values for particular features in samples are missing can be estimated (imputation) rather than thrown out for training of the model. As a result, the sample size N can be larger than shown in FIG. 9. For example, imputation on the data was performed to increase N to 1051.

A model may use 1 to 5, 6 to 10, 10 to 20, 20 to 50, 50 to 100, 100 to 200, or over 200 variables. The variables (i.e., features) may be any variable mentioned herein, including in any of the figures. The variables determined from training the model may be from a set of variables including 6 to 10, 10 to 20, 20 to 50, 50 to 100, 100 to 200, 200 to 500, 500 to 1,000, or over 1,000 variables. The variables in the set of variables may be any variable mentioned herein.

The top variables for different team sizes (i.e., variable selections of size m) are listed in FIGS. 10-14. A model may use any of these variables in any combination (or other variable combinations). FIGS. 11 and 13 have the same team sizes and 50 rounds of evaluation ("r"), but show different variables as a result of the randomized nature of the ranking algorithm.

The example four-variable TRAIL model was evaluated on the GOYA holdout datasets, which were associated with subjects not part of the training dataset.

IV.B. Clinical Validation using MAIN Dataset

The example four-variable TRAIL model was also evaluated on the MAIN dataset. Data for external validation were obtained from the multicenter, randomized, double-blind, placebo-controlled phase III MAIN study (NCT00486759). In total, 186 centers, located in 30 countries, participated in MAIN, and recruited subjects aged 18 years or older with previously untreated DLBCL between July 2007 and May 2010. This trial was designed to compare R-CHOP with and without bevacizumab. Investigators participating in MAIN at the study site level predefined subjects to follow a 14- or a 21-day cycle of CHOP chemotherapy. Treatment with additional bevacizumab was blinded by placebo infusions in addition to R-CHOP. Further details of study treatment were previously published in Seymour et al., R-CHOP with or without bevacizumab in patients with previously untreated diffuse large B-cell lymphoma: final MAIN study outcomes. *Haematologica*, 2014; 99(8):1343-1349, the contents of which are incorporated herein by reference for all purposes. The trial was stopped early by sponsor decision due to increased cardiotoxicity and no prolongation of progression-free survival (PFS) in the bevacizumab arm. The median duration of follow up for the R-CHOP and R-CHOP in combination with bevacizumab arms were 23.7 and 23.6 months, respectively. Due to the safety signals observed in the bevacizumab arm and the known increased toxicity associated with CHOP in 14-day cycles (CHOP-14), only data from subjects treated with R-CHOP for 21-day cycles (R-CHOP-21) in MAIN were used here for model validation.

IV.C. Different Model Validation Results

A set of models using certain variables was validated in two independent clinical studies. A composite binary endpoint was selected for analyzing the clinical studies. The endpoint was configured such that any of the following three events qualified: (1) adverse events (AEs) leading to withdrawal of cyclophosphamide and/or doxorubicin; (2) average relative dose intensity of cyclophosphamide and doxorubicin <80% across 6 cycles, not related to progressive disease (PD); or (3) death within the first 6 cycles not related to progressive disease (PD). The two independent clinical data sets used for validating the model are labeled GOYA Holdout (or similar) and MAIN R-CHOP-21 (or similar). The "Holdout" of GOYA Holdout refers to data that was not used for training the model.

Table 1 shows results of different models on the GOYA Training and GOYA Holdout data sets. The model is listed in the first column. The number of subjects n is in the second column. The cross validation area under the curve (CV AUC) is shown in the third column. The training data AUC is in the fourth column. The holdout data AUC is in the fifth column. The training AUC after fitting to full data is in the sixth column.

The rows show the three models used. The first model included the terms of equation (1): Creatinine Clearance (CRCL); Albumin (ALBUM); Charlson comorbidity index (CHARLSON); Heart, Vascular, and Diabetes Comorbidities (HVD); Bone Marrow Lymphocytes (BMLYMP); and BSA Corrected Creatinine Clearance (CRCLBSA). The second row is a model that excluded Bone Marrow Lymphocytes. The third model is a model that excluded Bone Marrow Lymphocytes and BSA Corrected Creatinine Clearance. The third model had the highest AUC for GOYA Holdout data.

TABLE 1

| Model | n | CV AUC | Training AUC | Holdout AUC | Training AUC after Fitting to Full Data |
|---|---|---|---|---|---|
| Including Bone Marrow Lymph | 742 | .749 | .755 | .614 | .723 |
| Excluding Bone Marrow Lymph | 1022 | .701 | .712 | .677 | .708 |
| Excluding Bon Marrow Lymph & BSA Corr. CRCL | 1022 | .686 | .700 | .722 | .707 |

The MAIN R-CHOP-21 data was from a study of bevacizumab (Avastin) in combination with Rituximab (MabThera) and CHOP (Cyclophosphamide, Hydroxydaunorubicin [Doxorubicin], Oncovin [Vincristine], Prednisone) chemotherapy in subjects with diffuse large B-cell lymphoma. This was a 2-arm study designed to compare the efficacy and safety of bevacizumab (Avastin) in combination with rituximab (MabThera) and CHOP (cyclophosphamide, hydroxydaunorubicin [doxorubicin], Oncovin [vincristine], prednisone) chemotherapy (R-CHOP) versus rituximab plus CHOP chemotherapy (R-CHOP) in previously untreated subjects with CD20-positive diffuse large B-cell lymphoma (DLBCL). Subjects were randomized to receive 8 cycles of treatment with R-CHOP plus bevacizumab or R-CHOP plus placebo. Treatment with bevacizumab/placebo and R-CHOP was given either on a 2-week or 3-week schedule and bevacizumab was given at a weekly average dose of 5 mg/kg (10 mg/kg for 2-week cycles and 15 mg/kg for 3-week cycles).

Table 2 shows results of different models on the MAIN R-CHOP-21 data set. The first column lists the model. The second column lists the AUC from a model fit to GOYA Training data. The third column lists the AUC when fitting the model to the full GOYA data (Training and Holdout). The rows show the three models used. The models involved the same terms as described with Table 1. MAIN R-CHOP-21 dataset did not have bone marrow lymphocyte measurements so there are no AUCs for the first model. The model excluding Bone Marrow Lymphocytes and BSA Corrected Creatinine Clearance had the highest AUC with either training data set.

TABLE 2

| Model | AUC When Fitting Model to Goya Training Data | AUC When Fitting Model to Goya Full Data |
| --- | --- | --- |
| Including Bone Marrow Lymph | NA | NA |
| Excluding Bone Marrow Lymph | .680 | .682 |
| Excluding Bone Marrow Lymph & BSA Corr. CRCL | .691 | .685 |

IV.D. Results with Four-Variable TRAIL Model

Figure 15:
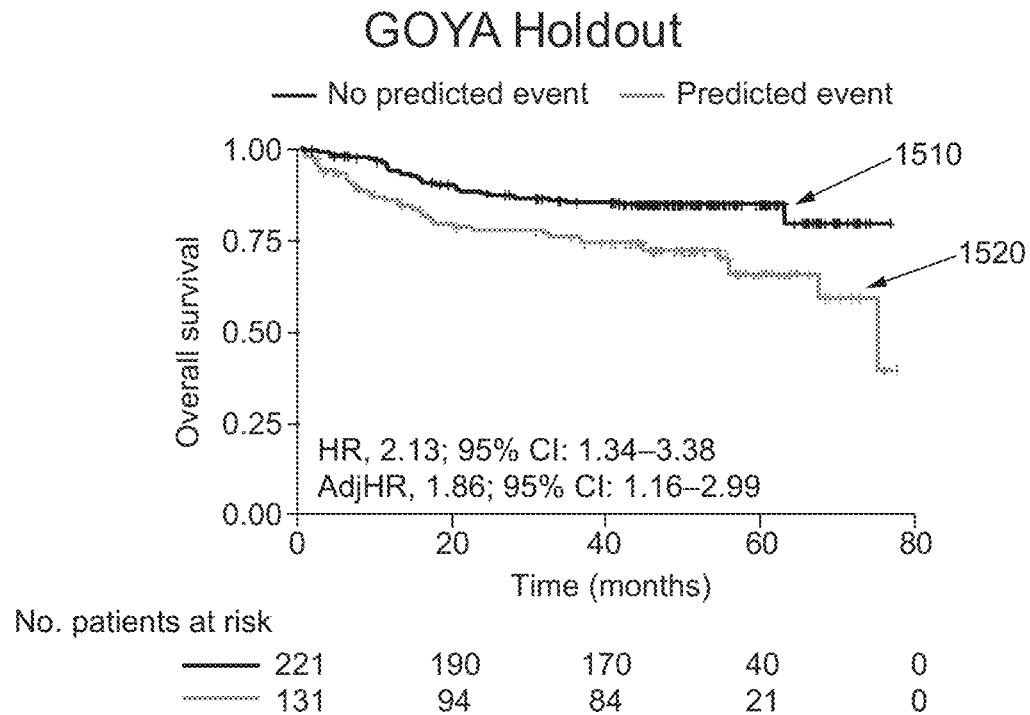
FIG. 15 shows the predictions for adverse events using a model with four variables on the GOYA Holdout data set according to some embodiments of the present disclosure.

FIG. 15 shows the predictions for composite endpoints using a model with four variables (Creatinine Clearance (CRCL); Albumin (ALBUM); Charlson comorbidity index (CHARLSON); Heart, Vascular, and Diabetes Comorbidities (HVD)). FIG. 15 uses the GOYA Holdout data set. The overall survival is on the y-axis, and the time in months is on the x-axis. The top line (line 1510) indicates no predicted event, and the bottom line (line 1520) indicates a predicted event. The number of those encountering a predicted event or no predicted event are listed in tabular format under the graph. FIG. 15 also indicates the hazard ratios (HR) for predicted tolerability event group relative to no predicted tolerability event group are shown. An adjusted hazard ratio for a baseline International Prognostic Index (IPI)>2 are presented. The cutoff for determining the prediction of a tolerability event was determined by finding the value that maximized the Youden index using the GOYA training data. FIG. 15 shows that those subjects with a predicted event had a lower overall survival rate than those subjects without a predicted event.

Figure 16:
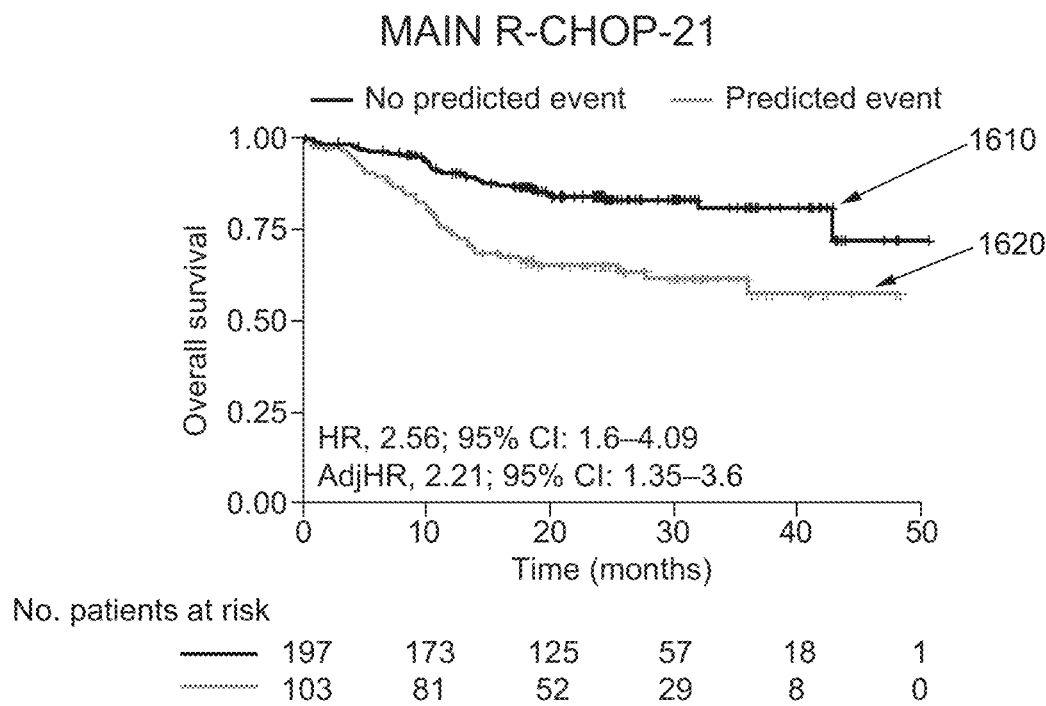
FIG. 16 shows the predictions for adverse events using a model with four variables on a MAIN R-CHOP-21 validation data set according to some embodiments of the present disclosure.

FIG. 16 shows the predictions for composite endpoints using an example TRAIL model with four variables. FIG. 16 presents the same types of results as FIG. 15 but for MAIN R-CHOP-21 data set. Line 1610 indicates no predicted event. Line 1620 indicates a predicted event. FIG. 16 shows that those subjects with a predicted event had a lower overall survival rate than those subjects without a predicted event.

Figure 17:
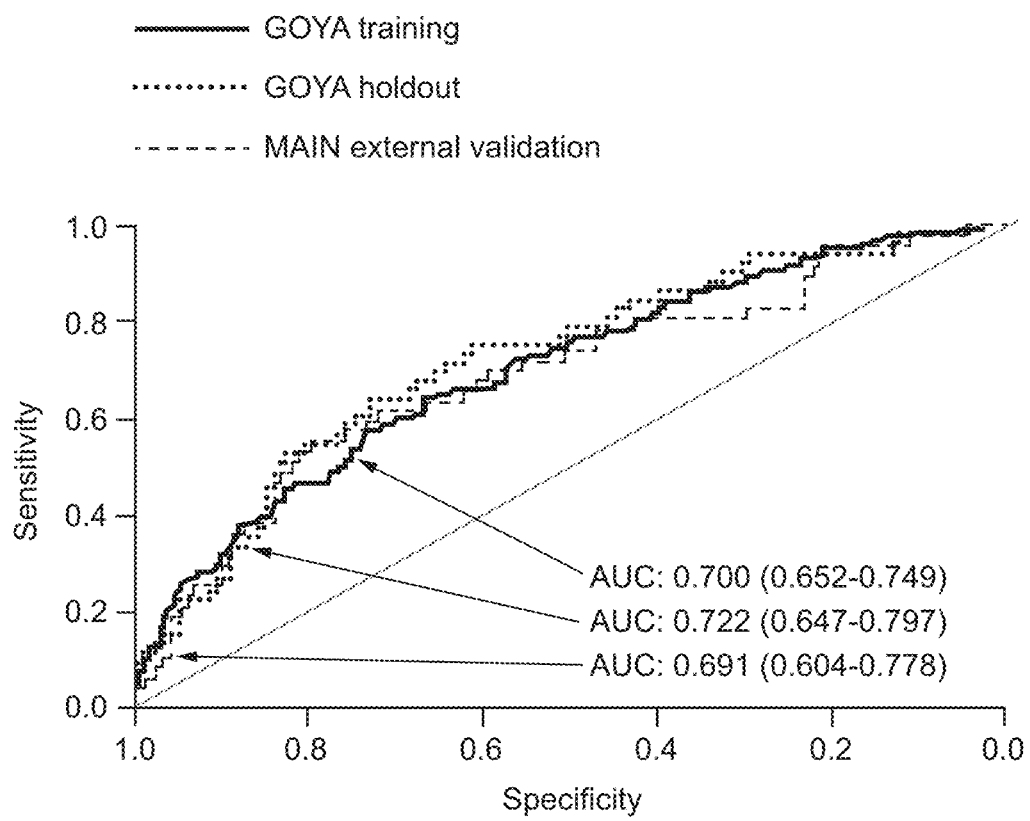
FIG. 17 shows ROC curves for an example TRAIL model using the GOYA training, GOYA holdout, and MAIN external validation data according to some embodiments of the present disclosure.

FIG. 17 shows ROC curves for the example TRAIL model with four variables using the GOYA training, GOYA holdout, and MAIN external validation data. The model reached an AUC (95% CI) of 0.700 (0.652-0.749) on the GOYA training data, 0.722 (0.647-0.797) on the GOYA holdout data, and 0.691 (0.604-0.778) on the MAIN external validation data.

Figures 18A, 18B:
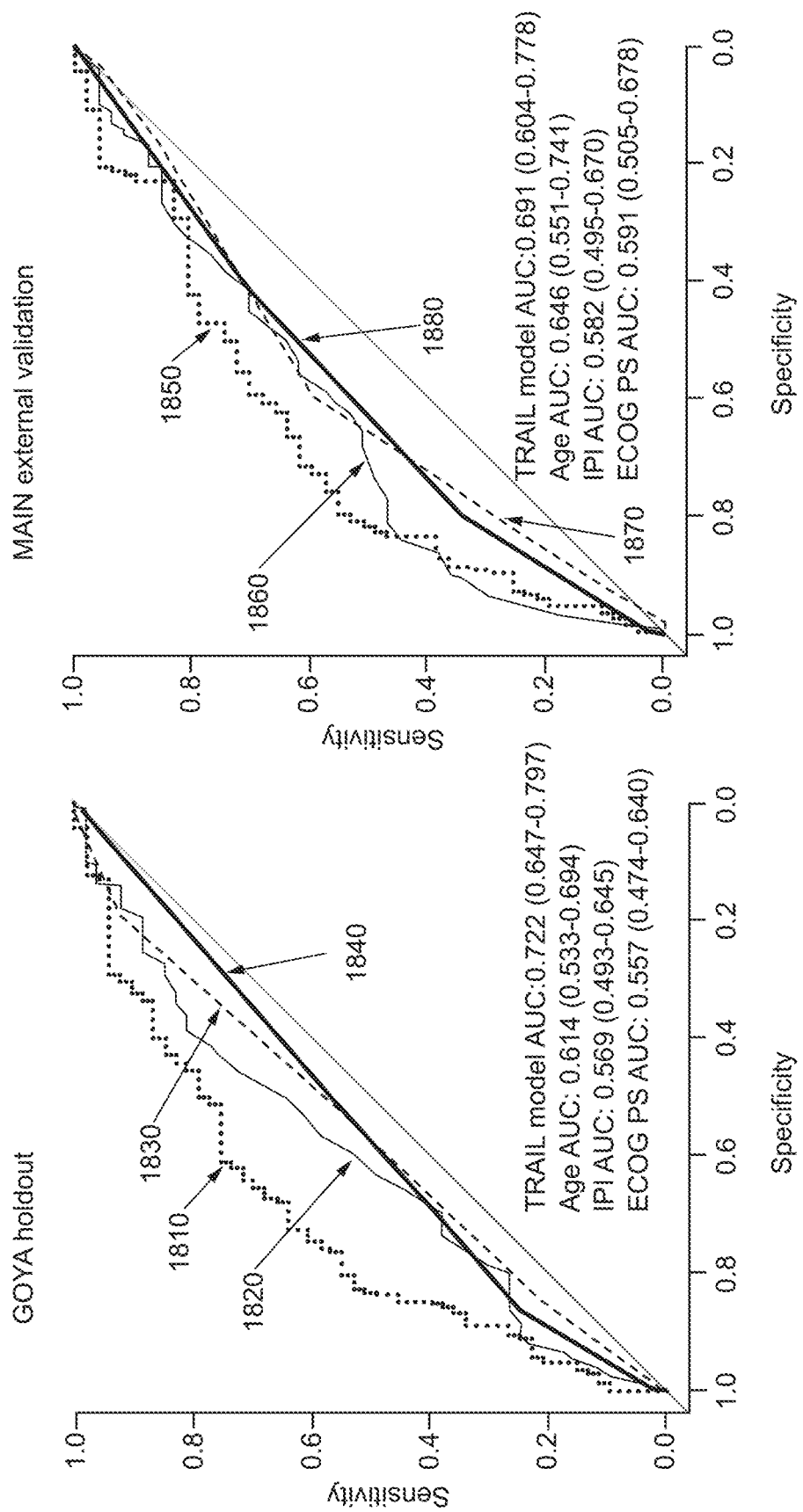
FIGS. 18A and 18B show ROC curves for an example TRAIL model compared with established prognostic factors using the GOYA holdout data and the MAIN external validation data according to some embodiments of the present disclosure.

FIG. 18A shows ROC curves for the example TRAIL model with four variables compared with established prognostic factors age, IPI, and ECOG PS (Eastern Cooperative Oncology Group Performance Status) using the GOYA holdout data. FIG. 18B shows ROC curves for the example TRAIL model compared with established prognostic factors age, IPI, and ECOG PS using the MAIN external validation. Lines 1810 and 1820 show the example TRAIL model. Lines 1820 and 1860 show age. Lines 1830 and 1870 show IPI. Lines 1830 and 1870 show ECOG PS. AUC was consistently higher for TRAIL models than for clinical risk factors expected to be associated with tolerability in both GOYA and MAIN.

In the GOYA holdout dataset, 74.1% of subjects reported a treatment emergent grade 3-5 AE in the high-risk category compared with 70.1% in the intermediate-risk, and 65.6% in the low-risk category. The corresponding proportions for MAIN were 74.0%, 57.5%, and 48.4% respectively. A greater proportion of subjects in the intermediate- and high-risk TRAIL categories experienced grade 4 and 5 AEs compared with the low-risk group.

IV.E. Cutoffs Based on Sensitivity or Specificity

Figure 19A:
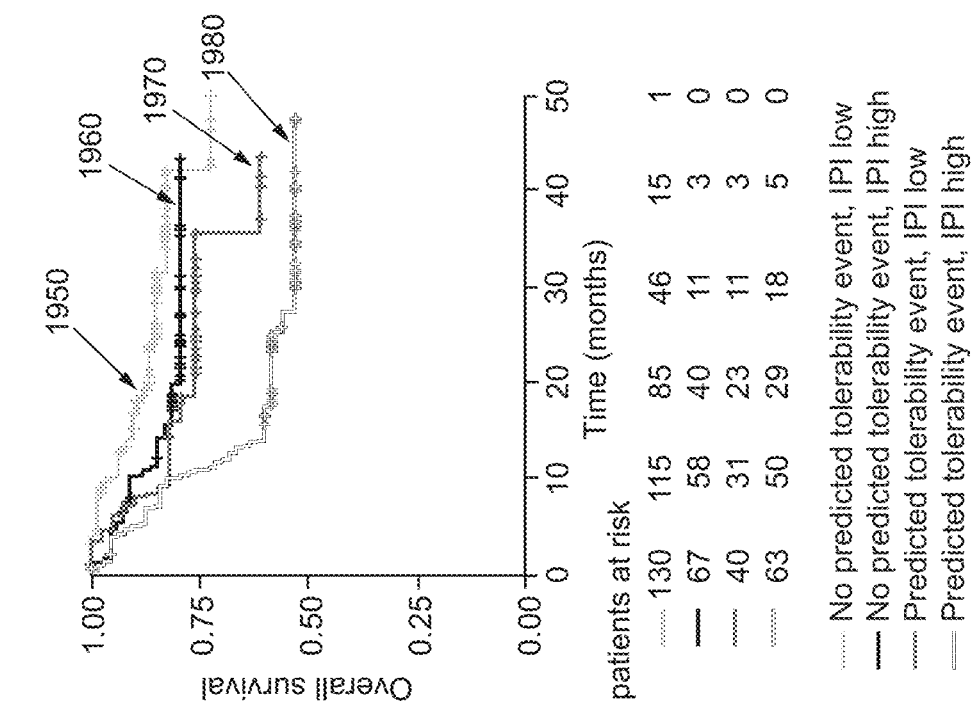
FIG. 19A and FIG. 19B show results of the model in combination with different IPI levels according to some embodiments of the present disclosure.
Figure 19B:
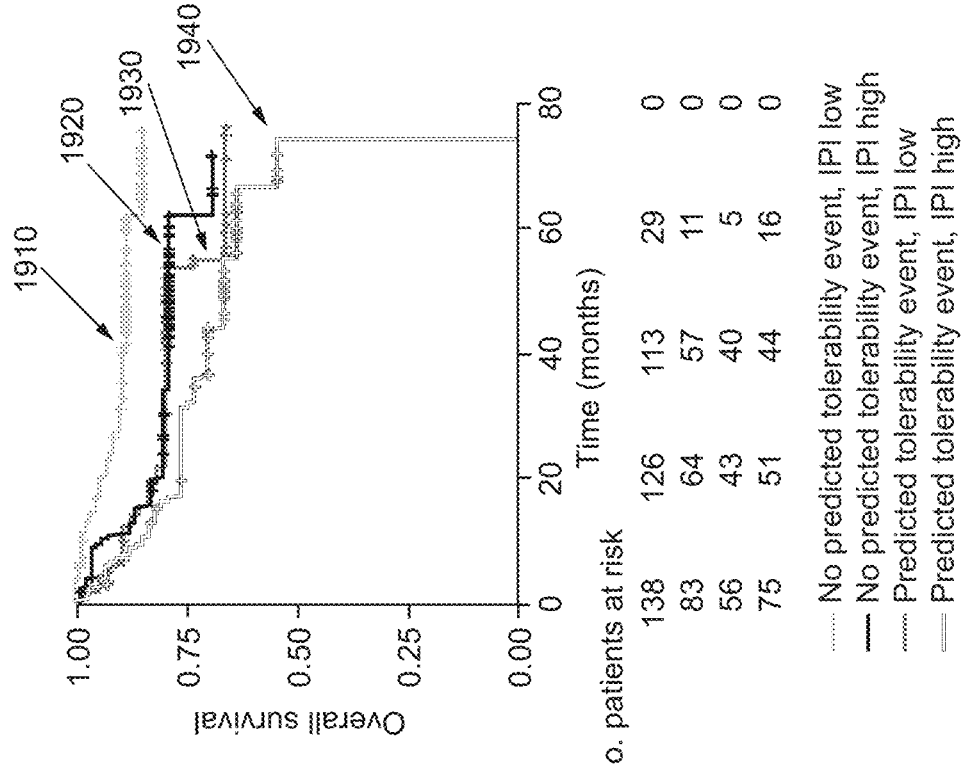

FIG. 19A and FIG. 19B show results of the example TRAIL model with four variables in combination with different IPI levels. FIG. 19A shows predicted survival for GOYA Holdout data, and FIG. 19B shows predicted survival for MAIN R-CHOP-21 data. The graphs present similar information as FIG. 15 and FIG. 16. However, four lines are presented instead of two lines. The red lines (lines 1910 and 1950) show no predicted tolerability event with a low IPI (IPI ≤2). The green lines (lines 1920 and 1960) show no predicted tolerability event with a high IPI (IPI >2). The blue lines (lines 1930 and 1970) show predicted tolerability event with a low IPI. The purple lines (lines 1940 and 1980) show a predicted tolerability event with a high IPI.

Cutoffs may be used to improve the prediction as to whether a particular subject will tolerate the particular treatment. A value exceeding the cutoff (e.g., above or below) may indicate that a subject is predicted to tolerate the particular treatment.

Table 3 shows the performance using cutoffs with the models using four variables (Creatinine Clearance (CRCL); Albumin (ALBUM); Charlson comorbidity index (CHARLSON); Heart, Vascular, and Diabetes Comorbidities (HVD)). The GOYA data set was used. The first column lists the criteria for the cutoff. The second and third columns are training scores. The second column lists the cutoff used. The third column lists the performance in terms of sensitivity and specificity. The fourth and fifth columns are CV scores. The fourth column lists the cutoff used. The fifth column lists the performance in terms of sensitivity and specificity.

The first row of data in Table 3 is for the criterion of maximizing the sum of sensitivity and specificity. The second row of data is for the criterion of setting the sensitivity to 0.80. The third row of data is for the criterion of setting the specificity to 0.80. The results show that cutoffs may be adjusted based on different criteria.

TABLE 3

| Criteria | Training scores | | CV scores | |
|---|---|---|---|---|
| | Cutoff | Perf | Cutoff | Perf |
| Sum of sens/spec | 0.126 | Sens = 65.2% Spec = 68.3% Spec = 42.6% | 0.1176 | Sens = 67.4% Spec = 64.3% |
| Sensitivity = 0.8 | 0.081 | Sens = 80.3% Spec = 42.2% | 0.07888 | Sens = 80.3% Spec = 42.2% |
| Specificity = 0.8 | 0.165 | Sens = 47.7% Spec = 80% | 0.165 | Sens = 44.7% Spec = 80% |

Figure 20:
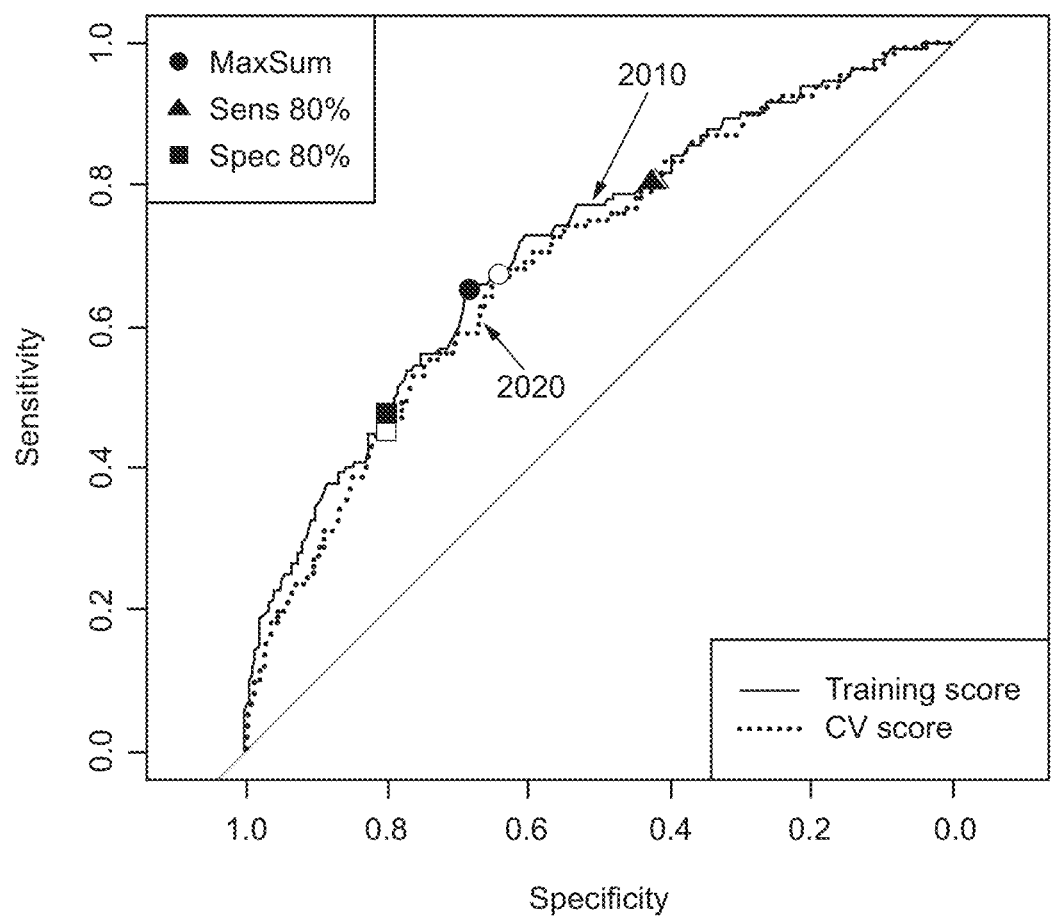
FIG. 20 shows an area under the curve graph for using cutoffs according to some embodiments of the present disclosure.

FIG. 20 shows an area under the curve graph for using cutoffs in Table 3. The two lines show the training score (line 2010) and the CV scores (line 2020). The labeled points are the sensitivities and specificities indicated in Table 3. Table 4 shows the performance of using cutoffs with the models using four variables (Creatinine Clearance (CRCL); Albumin (ALBUM); Charlson comorbidity index (CHARLSON); Heart, Vascular, and Diabetes Comorbidities (HVD)). The MAIN R-CHOP-21 data set was used. The first column lists the criteria for the cutoff. The second and third columns are CV scores (identical to Table 3). The fourth and fifth columns are for the MAIN R-CHOP-21 data set. The same criteria are used as in Table 4.

TABLE 4

| | | | MAIN | |
|---|---|---|---|---|
| | CV scores | | Perf with | 21 day cycles |
| Criteria | Cutoff | Perf | N = 376 | (N = 300) |
| Sum of sens/spec | 0.1176 | Sens = 67.4% Spec = 64.3% | Sens = 53.0% Spec = 72.6% | Sens = 59.6% Spec = 72.7% |
| Sensitivity = 0.8 | 0.07888 | Sens = 80.3% Spec = 42.2% | Sens = 75.8% Spec = 48.7% | Sens = 74.5% Spec = 49.8% |
| Specificity = 0.8 | 0.165 | Sens = 44.7% Spec = 80% | Sens = 33.3% Spec = 83.2% | Sens = 40.4% Spec = 83.0% |

IV.F. Cutoffs Based on Risk Percentiles

Figure 21:
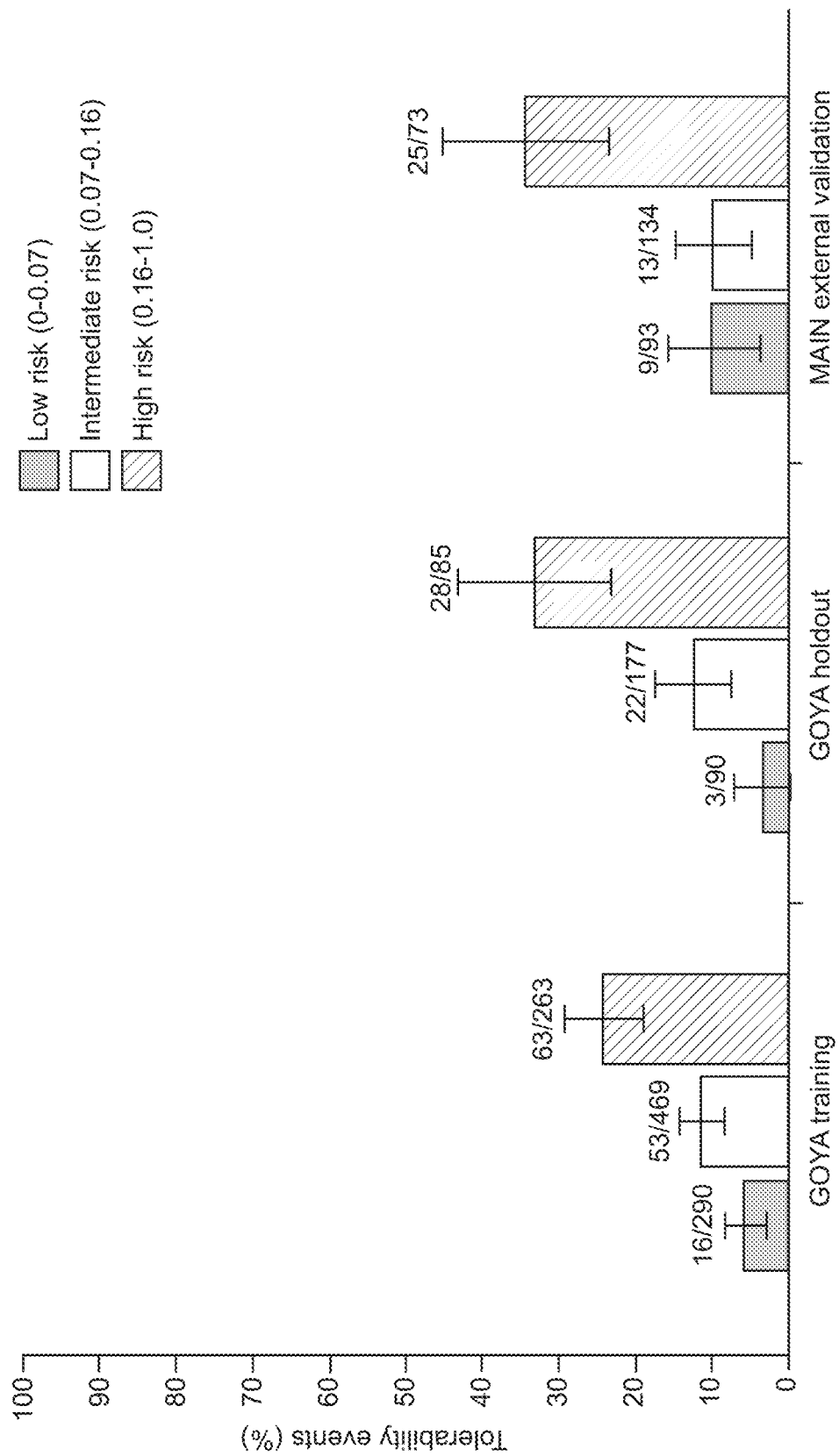
FIG. 21 shows the percentage of subjects experiencing a tolerability event by risk category according to some embodiments of the present disclosure.

FIG. 21 shows the percentage of subjects experiencing a tolerability event by risk category. Cutoffs for low-, intermediate-, and high-risk categories were defined based on quartiles of predicted probabilities (low risk [0, 0.07), intermediate risk [0.07, 0.16), and high risk [0.16, 1]. In the GOYA holdout dataset the proportion of subjects experiencing a tolerability event was 3.3% in the low-risk, 12.4% in the intermediate-risk and 32.9% in the high-risk group. The corresponding proportions for MAIN were 9.7%, 9.7% and 34.2%, respectively. FIG. 21 shows that a larger proportion of subjects having a higher predicted probability suffered an adverse event at a significantly higher rate than those with lower predicted probabilities. The cutoffs in FIG. 21 may be used for cutoff values described with process 100.

Figure 22A:
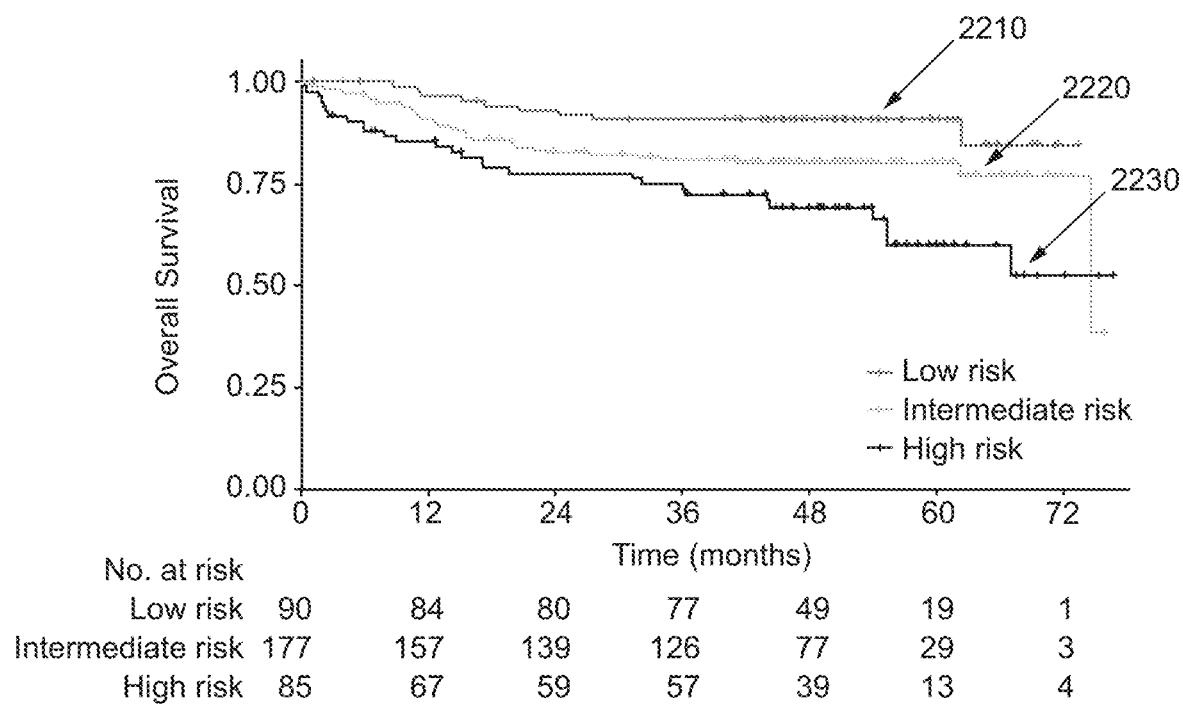
FIGS. 22A and 22B show Kaplan-Meier plots of overall survival stratified by risk category for the GOYA holdout dataset and the MAIN external validation data according to some embodiments of the present disclosure.
Figure 22B:
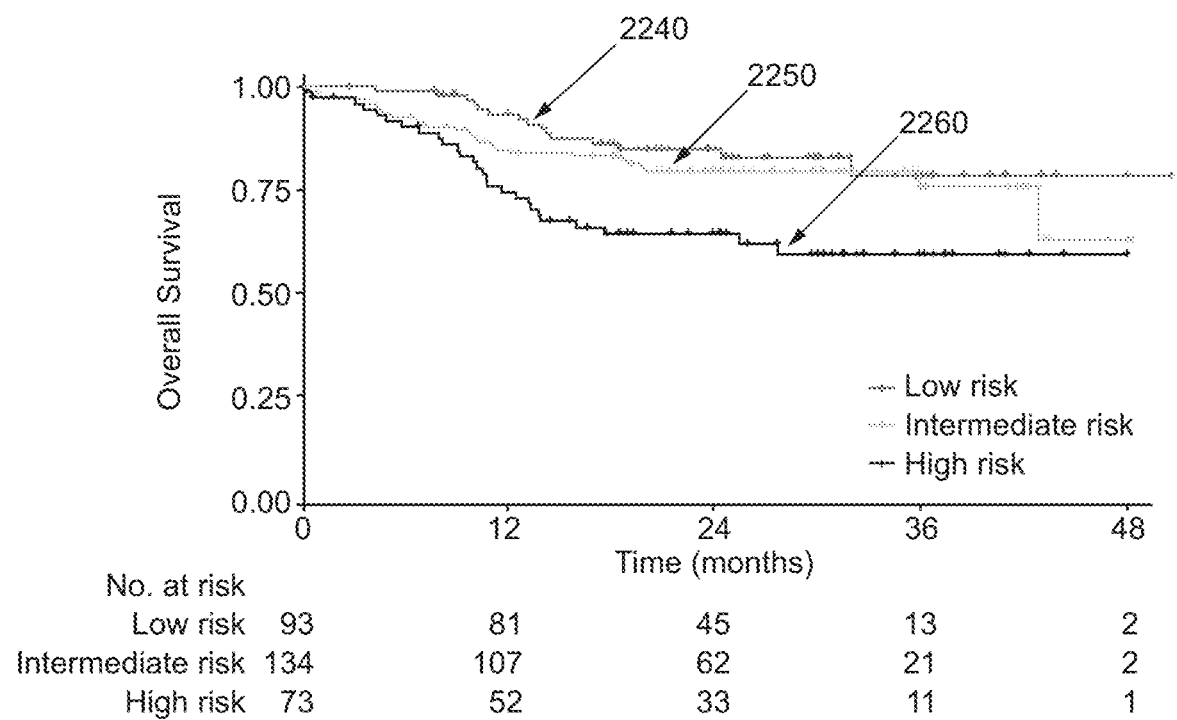

FIG. 22A shows Kaplan-Meier plots of overall survival stratified by risk category for the GOYA holdout dataset. FIG. 22B shows Kaplan-Meier plots of overall survival stratified by risk category for the MAIN external validation dataset. Lines 2210 and 2240 show low risk. Lines 2220 and 2250 show intermediate risk. Lines 2230 and 2260 show high risk. Similar to FIG. 21, FIGS. 22A and 22B show that those subjects categorized as high risk by the predicted probability tended to have a lower overall survival rate. The steeper drops in the overall survival rate at long times for intermediate risk (e.g., 72 months in FIG. 22A and 48 months in FIG. 22B) are artifacts resulting from small sample sizes.

The 4-year overall survival in the GOYA holdout dataset was 90.7% in the low-risk group, 80.2% in the intermediate-risk group, and 69.2% in the high-risk group.

In the GOYA holdout dataset, 74.1% of subjects reported a treatment emergent grade 3-5 AE in the high-risk category compared with 70.1% in the intermediate-risk, and 65.6% in the low-risk category. In the MAIN external validation dataset, the corresponding proportions for MAIN were 74.0%, 57.5%, and 48.4%, respectively. A greater proportion of subjects in the intermediate- and high-risk TRAIL categories experienced grade 4 and 5 AEs compared with the low-risk group.

IV.G. Real-World Data

Figure 23:
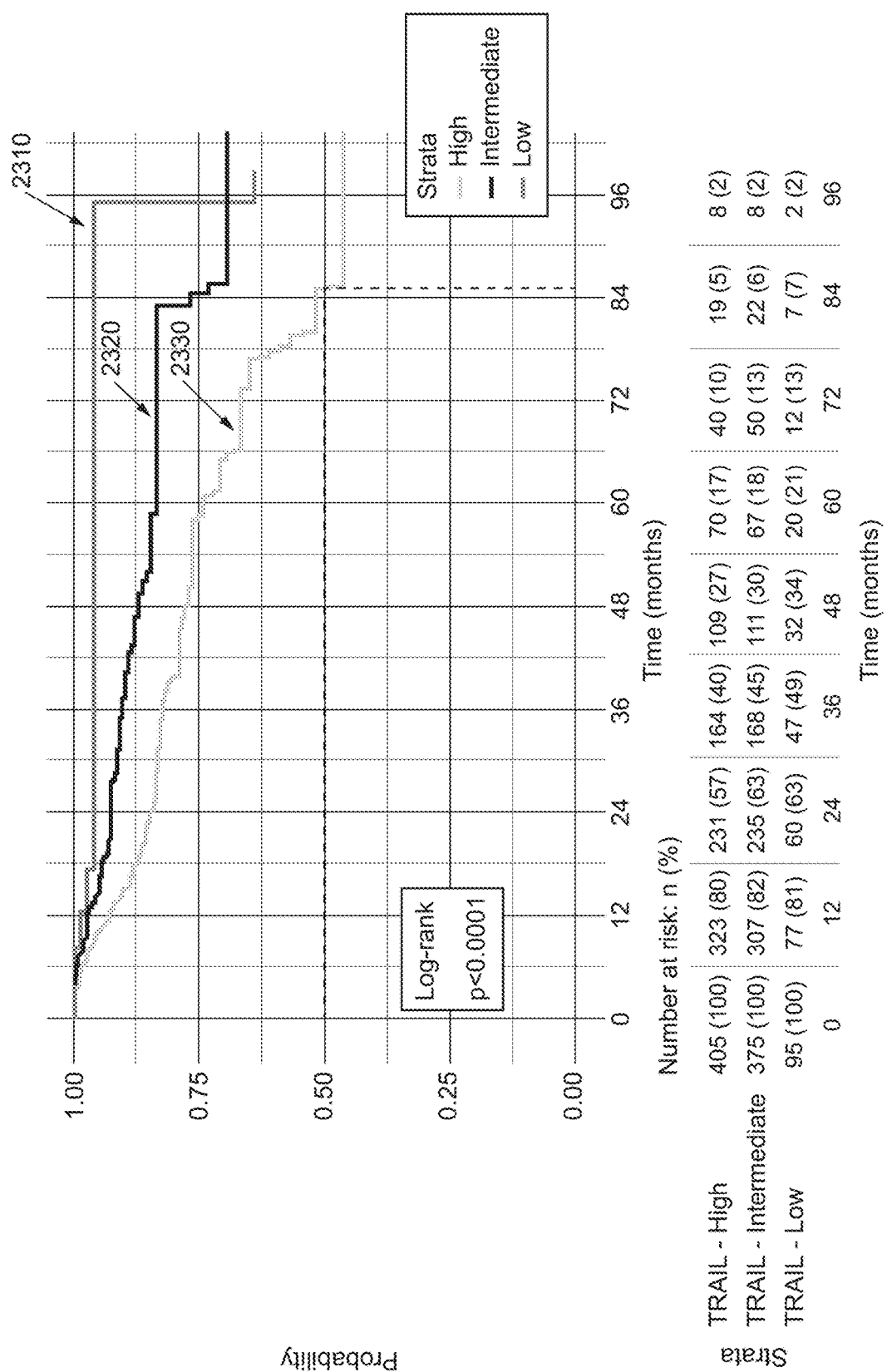
FIG. 23 shows Kaplan-Meier plot of overall survival stratified by risk category for the Flatiron RWD (real world data) data set according to some embodiments of the present invention.

FIG. 23 shows Kaplan-Meier plots of the overall survival rate for a real-world dataset, Flatiron RWD. The Flatiron RWD dataset was not a clinical study. The lines are divided by scores from the example TRAIL model with four variables, as with FIGS. 21, 22A, and 22B. Line 2310 shows subjects with scores corresponding with the lowest probability of an adverse event (highest predicted tolerability). Line 2320 shows subjects with scores corresponding with intermediate probability of an adverse event (intermediate predicted tolerability). Line 2330 shows subjects with scores corresponding to the highest probability of an adverse event (lowest predicted tolerability). Line 2330 shows that those with the lower predicted tolerability has the lowest overall survival rate. The steeper drops in the overall survival rate at long times (e.g., 96 months) are artifacts resulting from small sample sizes. FIG. 23 shows that the example four-variable TRAIL model can be applied to subjects in the real-world, outside of a clinical study. Other models developed by the TRAIL algorithm are also expected to be applied to real-world subjects.

VI. Terms

Table 5 includes terms used in the figures and other parts of the specification. Any of these terms may be variables in the machine-learning model described with FIGS. 1 and 2.

TABLE 5

| ABBREVIATION | VARIABLE |
|---|---|
| ALBUM | Albumin |
| ALKPH | Alkaline Phosphatase |
| ALT | SGPT/ALT |
| AP | Appetite Loss |
| AST | SGOT/AST |
| BANDS | Neutrophils, Bands, Abs |
| BANDSF | Neutrophils, Bands, Pct |
| BASOS | Basophils Abs |
| BASOSF | Basophils Pct |
| BICARB | Bicarbonate (CO2) |
| BMLYMP | Bone Marrow Lymphocytes Pct |
| BUN | Blood Urea Nitrogen |
| CALCUM | Calcium |
| CCI | Charlson Comorbidity Index |
| CHARLSON | Charlson Comorbidity Index |
| CD16 | CD16+ CD56+ |
| CD16LY | CD16+ CD56+/Lymphocytes |
| CD19 | CD19 |
| CD19LY | CD19/Lymphocytes |
| CD3 | CD3 |
| CD3LY | CD3/Lymphocytes |
| CF | Cognitive |
| CHLOR | Chloride |
| | Concomitant Medication (CM) Categories, ATC Codes, and GNE |
| CMCLASSCNT | Classification |
| CMCNT | Concomitant Medication (CM) Count |
| CO | Constipation |

TABLE 5-continued

| ABBREVIATION | VARIABLE |
|---|---|
| CRCL | Creatinine Clearance |
| CRCLBSA | BSA Corrected Creatinine Clearance |
| CREATN | Creatinine |
| CSFLDH | CSF Lactate Dehydrogenase |
| CSFLYMA | CSF Lymphocyte Abs |
| CTPROT | CSF Protein, Total |
| DI | Diarrhea |
| DIABETES2 | Indicator if medical history of diabetes mellitus, Type 2 diabetes mellitus, or type 1 diabetes mellitus |
| DY | Dyspnea |
| EF | Emotional |
| EOSIN | Eosinophils Abs |
| EOSINF | Eosinophils Pct |
| EXTRANODAL | Whether or not there was extranodal involvement spreading from the lymph nodes, eg. spleen, stomach, etc. |
| F13005 | CD3+ CD4+ |
| F13005LY | CD3+ CD4+/Lymphocytes |
| F13011 | CD3+ CD8+ |
| F13011LY | CD3+ CD8+/Lymphocytes |
| FA | Fatigue |
| FI | Financial Difficulties |
| HBCAB | Hepatitis B Virus Core Antibody |
| HBDNA | Hepatitis B Viral DNA |
| HBSAB | Hepatitis B Virus Surface Antibody |
| HBSAGC | Hepatitis B Surface Antigen, Char |
| HCAB | Hepatitis C Virus Antibody |
| HCRIT | Hematocrit |
| HCRNABC | Anti Hepatitis C RNA Antibody, Char |
| HGB | Hemoglobin |
| HTLV1AC | Anti Human T-lymphotrop Virus 1 AB, Char |
| HVD | Heart, Vascular, and Diabetes Comorbidities |
| IGA | Immunoglubulin A |
| IGG | Immunoglobulin G |
| IGM | Immunoglobulin M |
| LDH | Lactate Dehydrogenase |
| LYMMCE | Lymphoma Cells |
| LYMPH | Lymphocytes Abs |
| LYMPHF | Lymphocytes Pct |
| MHCNT | Medical History Terms Count to Calculate CCI/CHARLSON |
| MONOS | Monocytes Abs |
| MONOSF | Monocytes Pct |
| NAPTT | Non-Activated Partial Thromboplastin Tm |
| NEUTR | Neutrophils, Total, Abs |
| NEUTSA | Neutrophils, Segmented, Abs |
| NEUTSP | Neutrophils, Segmented, Pct |
| NV | Nausea and Vomiting |
| OTHCA | Other Cells, Abs |
| OTHCP | Other Cells, Pct |
| PA | pain |
| PF2 | Physical Functioning—Revised |
| PHOSAT | Phosphorus |
| PLATE | Platelet |
| POTAS | Potassium |
| PROTUR | Urine Protein, Char |
| PTINR | International Normalized Ratio |
| PTM | Prothrombin Time |
| PTR | Prothrombin Time Ratio |
| PTT | Activated Partial Thromboplastin Time |
| QL | Global Health/Quality of Life |
| QLQC30 | EORTC PRO questions |
| QLQC30_sf | EORTC PRO questions related to social functioning |
| R170898 | 1 Anti-RO5072759 Antibody |
| RBC | Red Blood Cell Count |
| RF2 | Role Functioning Revised Score |
| SF | Social Functioning |
| SL | insomnia |
| SODIUM | Sodium |
| SPREG | Serum Pregnancy Result |
| TBILI | Bilirubin |
| TPROT | Protein, Total |
| URACID | Uric Acid |
| WBC | White Blood Cell Count |

VI. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification, and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

All publications, patents, and patent applications cited herein are hereby incorporated by reference in their entirety for all purposes. None is admitted to be prior art.

What is claimed is:

1. A method comprising:
accessing an input data set that includes multiple input data values pertaining to a particular subject with lymphoma, each input data value corresponding to a variable of a set of variables, wherein the multiple input data values comprise an index value characterizing comorbidities of the particular subject;
inputting the input data set into a machine-learning model to generate a score corresponding to a degree to which the particular subject will tolerate a particular treatment to the lymphoma, wherein tolerating the particular treatment comprises not having the particular treatment ended or reduced below a threshold dose within a time period after starting the particular treatment, wherein the machine-learning model comprises:
a set of parameters determined using multiple training data elements, each of the multiple training data elements corresponding to a training subject with the lymphoma, and each of the multiple training data elements including a training input data set and a label, the label indicating a tolerance of the training subject to the particular treatment; and
a function relating received input data sets and the parameters to the score;
generating a prediction of the tolerance of the particular subject to the particular treatment using the generated score; and
administering (a) the particular treatment to the particular subject when the prediction of the tolerance is that the particular subject will tolerate the particular treatment, and (b) an alternative treatment to the particular subject when the prediction of the tolerance is that the particular subject will not tolerate or is unlikely to tolerate the particular treatment, wherein the particular treatment is R-CHOP (rituximab, cyclophosphamide, doxorubicin hydrochloride, vincristine, prednisolone), M-CHOP (mosuntuzumab with CHOP), or anti-CD20 treatment with CHOP.

2. The method of claim 1, wherein the set of variables comprises a result from a blood panel.

3. The method of claim 1, wherein the set of variables comprises a characterization of a medical history of the particular subject.

4. The method of claim 3, further comprising:
sending a request to a computing system storing the medical history of the particular subject,
receiving the medical history of the particular subject,
determining the index value characterizing the comorbidities of the particular subject.

5. The method of claim 1, wherein the set of variables comprises a result from an invasive diagnostic.

6. The method of claim 1, wherein the set of variables comprises an albumin concentration, a creatinine clearance, a comorbidity index, or a presence of cardiovascular or diabetes medical history.

7. The method of claim 6, wherein the set of variables further comprises a level of bone marrow lymphocytes.

8. The method of claim 1, wherein the set of variables comprises 5 or fewer variables.

9. The method of claim 1, wherein the set of variables comprises a level of hemoglobin, a red blood cell count, a hematocrit, concomitant medication count, a level of chloride, a total level of CD3 and CD4 protein complexes and T cell co-receptors, a level of lymphocytes, or a level of CD3 protein complex and T cell co-receptor.

10. The method of claim 1, wherein the lymphoma is diffuse large B-cell lymphoma, and the particular treatment comprises cyclophosphamide or doxorubicin hydrochloride.

11. The method of claim 1, further comprising using a blood panel to process a blood sample from the particular subject to determine one or more input data values of the multiple input data values.

12. The method of claim 1, wherein the time period is 18 weeks or less.

13. The method of claim 1, wherein the prediction is the particular subject is unlikely to tolerate the particular treatment.

14. The method of claim 1, further comprising:
comparing the score to a cutoff value, wherein the cutoff value is determined from a plurality of reference subjects, each reference subject of the plurality of reference subjects having a respective predicted score.

15. The method of claim 14, wherein the cutoff value is determined to achieve a predefined level of sensitivity or a predefined level of specificity for predicting the tolerance of the particular treatment in the plurality of reference subjects.

16. The method of claim 14, further comprising:
identifying a subset of the plurality of reference subjects, wherein a respective score of each reference subject in the subset is lower than a score of each reference subject in the plurality of reference subjects but not in the subset, and wherein a size of the subset corresponds to a predefined percentage relative to a size the plurality of reference subjects; and
defining the cutoff value as a given value that separates respective scores of reference subjects in the subset from scores of reference subjects in the plurality of reference subjects but not in the subset;
wherein comparing the score to the cutoff value comprises determining that the score exceeds the cutoff value, and the prediction is the particular subject is unlikely to tolerate the particular treatment.

17. The method of claim 13, further comprising in response to returning the prediction that the particular subject is unlikely to tolerate the particular treatment:
outputting a recommendation to enroll the particular subject in a clinical study including a treatment different than the particular treatment,
outputting a recommendation to treat the particular subject for lymphoma with another treatment different than the particular treatment, or
outputting a recommendation to not administer the particular treatment to the particular subject.

18. The method of claim 1, wherein the score is a probability of the particular subject tolerating the particular treatment.

19. A computer-program product tangibly embodied in a non-transitory machine-readable storage medium, including instructions configured to cause one or more data processors to perform a method comprising:
accessing an input data set that includes multiple input data values pertaining to a particular subject with lymphoma, each input data value corresponding to a variable of a set of variables, wherein the multiple input data values comprise an index value characterizing comorbidities of the particular subject;
inputting the input data set into a machine-learning model to generate a score corresponding to a degree to which the particular subject will tolerate a particular treatment to the lymphoma, wherein tolerating the particular treatment comprises not having the particular treatment ended or reduced below a threshold dose within a time period after starting the particular treatment, wherein the machine-learning model comprises:
a set of parameters determined using multiple training data elements, each of the multiple training data elements corresponding to a training subject with the lymphoma, and each of the multiple training data elements including a training input data set and a label, the label indicating a tolerance of the training subject to the particular treatment;
a function relating received input data sets and the parameters to the score; and
generating a prediction of the tolerance of the particular subject to the particular treatment using the generated score; and triggering administering (a) the particular treatment to the particular subject when the prediction of the tolerance is that the particular subject will tolerate the particular treatment, and (b) an alternative treatment to the particular subject when the prediction of the tolerance is that the particular subject will not tolerate or is unlikely to tolerate the particular treatment, wherein the particular treatment is R-CHOP (rituximab, cyclophosphamide, doxorubicin hydrochloride, vincristine, prednisolone), M-CHOP (mosuntuzumab with CHOP), or anti-CD20 treatment with CHOP.

20. A system comprising:
the computer-program product of claim 19; and
the one or more data processors.

* * * * *